(12) United States Patent
Aharonowitz et al.

(10) Patent No.: US 6,767,536 B1
(45) Date of Patent: Jul. 27, 2004

(54) RECOMBINANT STAPHYLOCOCCUS THIOREDOXIN REDUCTASE AND INHIBITORS THEREOF USEFUL AS ANTIMICROBIAL AGENTS

(75) Inventors: Yair Aharonowitz, Hod Hasharon (IL); Ilya Borovok, Ariel (IL); Gerald Cohen, Raanana (IL); Orit Uziel, Kfar-Saba (IL); Leonard Katz, Oakland, CA (US)

(73) Assignee: Ramot at Tel Aviv University Ltd., Tel Aviv (IL)

( * ) Notice: Subject to any disclaimer, the term of this patent is extended or adjusted under 35 U.S.C. 154(b) by 0 days.

(21) Appl. No.: 09/261,301

(22) Filed: Mar. 2, 1999

Related U.S. Application Data

(60) Provisional application No. 60/076,525, filed on Mar. 2, 1998.

(51) Int. Cl.[7] .................. A01N 63/00; A61K 38/54; A61K 39/40; A61K 39/00; A61K 39/09
(52) U.S. Cl. ............... 424/93.42; 424/94.1; 424/139.1; 424/165.1; 424/185.1; 424/237.1; 424/243.1; 435/7.33; 435/7.7; 435/36; 435/91.1; 435/91.5; 435/91.51; 935/9; 935/10; 935/11; 935/14
(58) Field of Search .................. 424/93.42, 94.1, 424/139.1, 165.1, 185.1, 237.1, 243.1; 435/7.33, 7.7, 36, 91.1, 91.5, 91.51; 935/9, 10, 11, 14

(56) References Cited

FOREIGN PATENT DOCUMENTS

| EP | 786519 A2 * | 7/1997 |
|---|---|---|
| WO | 97/23628 | 7/1997 |

OTHER PUBLICATIONS

Arscott et al. 1997. PNAS. 94:3621–3626.*
Ji et al. 1994. Biochemistry. 7294–7299.*
Holmgren, et al., "Thioredoxin and Thioredoxin Reductase", Methods in Enzymology, vol. 252 (1995) pp 199–.
Sequence Database EMBL ID 054079.
Sequence Database EMBL ID SAAJ3781.
Aharonowitz, et al., "Characterization of a Broad–Range Disulfide Reductase from *Streptomyces clavuligerus*, et al.", Journal of Bacteriology, vol. 175, No. 3, 1993, pp. 623–629.
Arscott, et al., "The mechanism of thioredoxin reductase from human placenta", et al., Proc. Natl. Acad. Sci. USA, vol. 94, 1997, pp. 3621–3626.
Chae, et al., "Thioredoxin–dependent Peroxide Reductase from Yeast", The Journal of Biological Chemistry, vol. 269, No. 44, 1994, pp. 27670–27678.
Cohen, et al., "Thioredoxin–Thioredoxin Reductase System of *Streptomyces clavuligerus*, et al.", Journal of Bacteriology, vol. 175, 1993, pp. 5159–5167.
Cohen, et al. "The Thioredoxin System of *Penicillium chrysogenum*, et al.", Journal of Bacteriology, vol. 176, 1994, pp. 973–984.
Dai, et al., "Crystal Structure of *Arabidopsis thaliana* NADPH, et al.", Journal of Molecular Biology, vol. 264, 1996, pp. 1044–1057.
Holmgren, A., "Bovine Thioredoxin System", The Journal of Biological Chemistry, vol. 252, 1997, pp. 4600–4606.
Lubbers, et al., "Components of glycine reductase from *Eubacterium acidaminophilum*, et al.", European Journal of Biochemistry, vol. 217, 1993, pp. 791–798.
Luthman, et al. "Rat Liver Thioredoxin and Thioredoxin Reductase, et al." Biochemistry, vol. 21, 1982, pp. 6628–6633.
Russell, et al., "Sequence of Thioredoxin Reductase from *Escherichia coli*". The Journal of Biological Chemistry, vol. 263, 1988, pp. 9015–9019.

* cited by examiner

*Primary Examiner*—Mark Navarro
*Assistant Examiner*—Ja-Na Hines
(74) *Attorney, Agent, or Firm*—Winston & Strawn LLP

(57) ABSTRACT

Isolated and purified Staphylococcus thioredoxin reductases (TrxB) are provided. Polynucleotides encoding the TrxBs, vectors and host cells containing such polynucleotides are also provided. In addition, antibodies reactive with the TrxBs are provided, as are methods of isolating the TrxBs, as well as methods for producing recombinant TrxBs, using TrxBs for screening compounds for TrxB-modulating activity, and detecting Staphylococcus in a test sample.

8 Claims, 9 Drawing Sheets

| | | | | |
|---|---|---|---|---|
|ATGACTGAAA|TAGATTTTGA|TATAGCAATT|ATCGGTGCAG|GTCCAGCTGG|50
|TATGACTGCT|GCAGTATACG|CATCACGTGC|TAATTTAAAA|ACAGTTATGA|100
|TTGAAAGAGG|TATTCCAGGC|GGTCAAATGG|CTAATACAGA|AGAAGTAGAG|150
|AACTTCCCTG|GTTTCGAAAT|GATTACAGGT|CCAGATTTAT|CTACAAAAAT|200
|GTTTGAACAC|GCTAAAAAGT|TTGGTGCAGT|TTATCAATAT|GGAGATATTA|250
|AATCTGTAGA|AGATAAAGGC|GAATATAAAG|TGATTAACTT|TGGTAACAAA|300
|GAATTAACAG|CTAAAGCGGT|CATTATTGCT|ACAGGTGCAG|GATACAAGAA|350
|AATTGGTGTT|CCGGGTGAAC|AAGAACTTGG|TGGACGCGGT|GTAAGTTATT|400
|GTGCAGTATG|TGATGGTGCA|TTCTTTAAAA|ATAAACGCCT|ATTCGTTATC|450
|GGTGGTGGTG|ACTCAGCAGT|AGAAGAGGGA|ACATTCTTAA|CTAAATTTGC|500
|TGACAAAGTA|ACAATCGTTC|ACCGTCGTGA|TGAGTTACGT|GCACAACGTA|550
|TTTTACAAGA|TAGAGCATTC|AAAAATGATA|AATAGACTT|TATTTGGAGC|600
|CATACTTTGA|AATCAATTAA|TGAAAAAGAC|GGCAAAGTGG|GTTCTGTGAC|650
|ATTAACGTCT|ACAAAAGATG|GTTCAGAAGA|AACACACGAG|GCTGATGGTG|700
|TATTCATCTA|TATTGGTATG|AAACCATTAA|CAGCACCATT|TAAAGACTTA|750
|GGTATTACAA|ATGATGTTGG|TTATATTGTG|ACAAAAGATG|ATATGACAAC|800
|ATCAGTACCA|GGTATTTTTG|CAGCAGGAGA|TGTTCGCGAC|AAAGGTTTAC|850
|GCCAAATTGT|CACTGCTACT|GGCGATGGTA|GTATTGCAGC|ACAAAGTACG|900
|AGCGGATATA|TTGAACATTT|AAACGATCAA|GCTAA| |936

FIG.1

```
MTEIDFDIAI  IGAGPAGMTA  AVYASRANLK  TVMIERGIPG  GQMANTEEVE   50
NFPGFEMITG  PDLSTKMFEH  AKKFGAVYQY  GDIKSVEDKG  EYKVINFGNK  100
ELTAKAVIIA  TGAGYKKIGV  PGEQELGGRG  VSYCAVCDGA  FFKNKRLFVI  150
CCCDSAVEEG  TFLTKFADKV  TIVHRRDELR  AQRILQDRAF  KNDKIDFIWS  200
HTLKSINEKD  GKVGSVTLTS  TKDGSEETHE  ADGVFIYIGM  KPLTAPFKDL  250
GITNDVGYIV  TKDDMTTSVP  GIFAAGDVRD  KGLRQIVTAT  GDGSIAAQST  300
SGYIEHLNDQ  A                                              311
```

FIG.2

```
  1 ATGACTGAAG TAGATTTTGA TGTAGCAATA ATCGGTGCAG GTCCTGCCGG
 51 TATGACAGCA GCAGTATATG CATCTCGTGC CAATTTAAAA ACTGTCATGA
101 TTGAACGCGG TATGCCAGGC GGTCAAATGG CAAACACTGA AGAAGTAGAG
151 AATTTTCCAG GATTTGAGAT GATCACAGGT CCTGACTTAT CTACTAAAAT
201 GTTTGAACAT GCTAAAAAAT TTGGTGCGGA ATACCAATAT GGCGATATTA
251 AATCTGTTGA AGATAAAGGC GACTATAAAG TTATCAATTT AGGGAATAAA
301 GAGATAACAG CACATGCAGT TATTATCTCA ACTGGAGCAG AGTATAAAAA
351 GATTGGCGTT CCTGGTGAAC AAGAATTAGG AGGACGTGGA GTAAGTTATT
401 GTGCGGTTTG TGATGGAGCA TTCTTTAAAA ATAAACGTCT TTTCGTAATT
451 GGCGGCGGAG ATTCAGCGGT AGAAGAAGGT ACTTTCTTAA CTAAATTTGC
501 AGATAAAGTA ACGATTGTTC ACCGTAGAGA TGAATTACGT GCACAAAACA
551 TCTTGCAAGA ACGTGCCTTC AAAAATGATA AGTTGACTT TATTTGGAGT
601 CATACACTTA AAACAATTAA TGAAAAAGAT GGTAAAGTTG GTTCAGTTAC
651 ACTTGAATCA ACTAAAGATG GTGCTGAACA GACTTATGAT GCCGACGGTG
701 TATTCATTTA TATTGGAATG AAACCACTCA CAGCACCATT TAAAAATCTT
751 GGTATTACAA ATGACGCGGG ATACATTGTC ACACAAGATG ACATGAGTAC
801 TAAAGTACGA GGTATTTTTG CTGCAGGTGA CGTTCGTGAT AAAGGGTTAC
851 GTCAAATTGT TACTGCTACA GGAGACGGTA GTATTGCGGC TCAAAGTGCA
901 GCTGATTATA TTACAGAATT AAAAGATAAT TAA
                                      STOP
```

FIG.6

```
TrxB_Sa   MTEIDFDIAIIGAGPAGMTAAVYASRANLKTVMIERGIPGGQMANTEEVE    50
          |||:|||:||||||||||||||||||||||||||| -|||||||||||||
TrxB_Se   MTEVDFDVAIIGAGPAGMTAAVYASRANLKTVMIERGMPGGQMANTEEVE    50

TrxB_Sa   NFPGFEMITGPDLSTKMFEHAKKFGAVYQYGDIKSVEDKGEYKVINFGNK   100
          |||||||||||||||||||||||||| |||||||||||||:||||  |||
TrxB_Se   NFPGFEMITGPDLSTKMFEHAKKFGAEYQYGDIKSVEDKGDYKVINLGNK   100

TrxB_Sa   ELTAKAVIIATGAEYKKIGVPGEQELGGRGVSYCAVCDGAFFKNKRLFVI   150
          |:|| ||||-||||||||||||||||||||||||||||||||||||||||
TrxB_Se   EITAHAVIISTGAEYKKIGVPGEQELGGRGVSYCAVCDGAFFKNKRLFVI   150

TrxB_Sa   GGGDSAVEEGTFLTKFADKVTIVHRRDELRAQRILQDRAFKNDKIDFIWS   200
          ||||||||||||||||||||||||||||||| |||:||||||:|||||
TrxB_Se   GGGDSAVEEGTFLTKFADKVTIVHRRDELRAQNILQERAFKNDKVDFIWS   200

TrxB_Sa   HTLKSINEKDGKVGSVTLTSTKDGSEETHEADGVFIYIGMKPLTAPFKDL   250
          ||||-||||||||||||| |||||-|:|::||||||||||||||||| -|
TrxB_Se   HTLKTINEKDGKVGSVTLESTKDGAEQTYDADGVFIYIGMKPLTAPFKNL   250

TrxB_Sa   GITNDVGYIVTKDDMTTSVPGIFAAGDVRDKGLRQIVTATGDGSIAAQSA   300
          ||||| |||||-|||-| | |||||||||||||||||||||||||||||
TrxB_Se   GITNDAGYIVTQDDMSTKVRGIFAAGDVRDKGLRQIVTATGDGSIAAQSA   300

TrxB_Sa   AEYIEHLNDQA   311
          |:||   | |
TrxB_Se   ADYITELKDN*  311
```

FIG.7

RECOMBINANT STAPHYLOCOCCUS THIOREDOXIN REDUCTASE AND INHIBITORS THEREOF USEFUL AS ANTIMICROBIAL AGENTS

This application claims priority to the provisional application Serial No. 60/076,525 filed on Mar. 2, 1998.

TECHNICAL FIELD

This invention relates generally to microbial metabolism and antimicrobial therapeutic agents. In particular, the invention relates to the bacterial enzyme thioredoxin reductase, to compounds that inhibit this enzyme, and to the use of these compounds as antimicrobial agents, particularly for the therapy of infections caused by Staphylococcus spp.

BACKGROUND OF THE INVENTION

The thioredoxin system is composed of NADPH, thioredoxin (Trx) and the flavoenzyme thioredoxin reductase (TrxB). Trx reduction by TrxB involves two half-reactions. In the first half-reaction, the FAD prosthetic group of TrxB is reduced by NADPH and electrons are transferred to cysteines present in the active site of TrxB. In the second half-reaction, oxidized Trx is reduced by TrxB. The thioredoxin system serves to transfer reducing equivalents for reductive enzymes such as ribonucleotide reductase, methionine sulfoxide reductase and vitamin K epoxide reductase. It also mediates protein folding and exerts specific redox control of some transcription factors to modulate their binding to DNA.

The thioredoxin system is of particular importance for redox metabolism in some Gram-positive bacteria. In this regard, certain Gram-positive bacteria, such as staphylococci, lack detectable glutathione (GSH) and glutathione reductase (GSR) which together play a key role in maintaining intracellular thiol-disulfide balance. GSH is the predominant thiol produced by aerobic eukaryotes and some Gram-positive bacteria, is believed to protect aerobic organisms from oxygen toxicity, and participates in a multitude of functions. For example, GSH plays a pivotal role in management of oxidative stress and maintenance and regulation of the redox balance. It acts as a cofactor for peroxide and ribonucleotide reductions, and serves in the conjugation and detoxification of foreign substances. Most organisms contain millimolar intracellular concentrations of GSH which, in concert with GSR and glutathione peroxidase, governs the redox status of the cellular environment. Thus, in microorganisms lacking the glutathione system, such as *Staphylococcus aureus*, the thioredoxin system, which is able to substitute for some of the glutathione-dependent processes, is of utmost importance.

The TrxB component of the thioredoxin system is a FAD-containing enzyme and belongs to a family of pyridine nucleotide-disulfide oxidoreductases. The bacterial enzyme obtained from *Streptomyces clavuligerus*, is a homodimer of 35 kDa subunits and has a native molecular weight of approximately 70 kDa. Aharonowitz et al. (1993) *J. Bacteriol.* 175:623–629. Each subunit of TrxB contains NADPH- and FAD-binding domains and includes an oxidoreductase active dithiol in the conserved sequence -CAT/VC-. Since the cysteine residues of TrxB are relatively inaccessible to the substrate thioredoxin, the enzyme appears to undergo a large conformational change during catalysis.

TrxBs from different mammalian species including calf (Holmgren, A. (1997) *J. Biol. Chem.* 252:4600–4606), rat (Luthman et al. (1982) *Biochem.* 21:66628–6633), and human (Arscott, et al. (1997) *Proc. Natl. Acad. Sci. USA* 94:3621–3626), have been purified and biochemically characterized. The rat liver TrxB has been isolated as a 116 kDa homodimer of 58 kDa subunits, and the mass of human placental TrxB estimated to be 160 kDa by gel-filtration chromatography and 130 kDa (two 65 kDa subunits) by sucrose density gradient centrifugation. The size difference between human TrxB and the smaller bacterial TrxBs is primarily due to differences in the dimer-interface domain. The redox-active cysteines of human TrxB are located in the FAD domain with a 4-amino acid bridge linking the two cysteines. The active-site disulfide of bacterial TrxBs, on the other hand, is located within the NADPH domain and a 2-amino acid bridge links the two cysteines. The 3D structure of the human TrxB is likely to be more similar to GSR than to the bacterial TrxB. Thus, primary amino acid sequence alignment of human TrxB with bacterial TrxB sequences reveals just 23–31% identity, whereas alignment of the human TrxB with GSRs of different sources shows 35–44% identity. Arscott, et al. (1997) *Proc. Natl. Acad. Sci. USA* 94:3621–3626.

Based on the significant differences that exist between the bacterial and the mammalian trxB genes, and the enzymes encoded thereby, the bacterial TrxB provides a potential target for the development of novel antibacterial drugs with a high degree of selectivity.

Antimicrobial agents commonly used to combat bacterial infections generally interfere with one or more critical steps in the metabolism of the bacterium, resulting in growth inhibition or death of the microbe. However, pathogenic microorganisms, including staphylococci, are developing resistance, and in many cases multiple resistances, to existing antimicrobial agents. In this regard, *S. aureus* is an opportunistic pathogen of increasing medical concern. It can be aggressively invasive, spreading rapidly through soft tissues, directly invading bones and even entering the bloodstream to produce septic shock and disseminated intravascular coagulation. Infections caused by staphylococci generally fall within one of two categories: those related to toxins produced by the bacterium exclusively, including gastroenteritis, toxic shock syndrome, scalded skin syndrome, and the like; and those related to direct invasion and systemic spread of the organism, including dermal infections, bone and joint infections, staphylococcal pneumonia and empyema, meningitis, cerebritis, endocarditis, bacteremia, septic shock, and the like.

These staphylococcal infections have traditionally been treated with $\beta$-lactam antibiotics. However, strains of $\beta$-lactam antibiotic-resistant staphylococci (BLARS), such as methicillin-resistant *S. aureus* (MRSA), have developed and become a widespread cause of fatal nosocomial infection. Infections caused by such resistant staphylococci are treated predominantly with "last resort" antibiotics such as vancomycin. Since resistance to these antibiotics would essentially exhaust the current therapeutic arsenal, it is essential that new antibacterial agents be identified.

SUMMARY OF THE INVENTION

The inventors herein have identified a bacterial thioredoxin reductase (TrxB) from Staphylococcus spp. that catalyzes, in two half-reactions, the specific NADPH-dependent reduction of thioredoxin (Trx), with the concomitant oxidation of NADPH to NADP$^+$. In the first half-reaction, the FAD prosthetic group of TrxB is reduced by NADPH and electrons are transferred to cysteines present in the active site of TrxB. In the second half-reaction, oxidized Trx is reduced by TrxB.

The thioredoxin system provides a significant metabolic function in staphylococci and other Gram-positive bacteria that do not produce glutathione (GSH). The thioredoxin system catalyzes a broad range of protein thiol-disulfide exchange reactions, donates hydrogen for ribonucleotide reductase which is an essential enzyme in DNA synthesis, and is involved in redox regulation of numerous enzyme activities.

Staphylococcal TrxB differs significantly in its function from that of the mammalian enzyme in two important ways. First, it operates in an intracellular environment lacking GSH and GSH-dependent reductases. Second, its subunits are appreciably smaller than the mammalian enzyme and the dimeric enzyme possesses a substrate specificity distinct from its mammalian counterpart. Inhibition of Staphylococcal TrxB activity may cause depletion of reduced low molecular weight thiols, increase protein thiol oxidation, and interfere with DNA synthesis and radical scavenging. Such compromised cells are more likely to succumb to environmental challenges, such as those posed by the host immune system.

Consequently, bacterial TrxB provides an excellent target for the development of novel antibacterial drugs with a high degree of selectivity.

Such antibacterials act by inhibiting TrxB, thereby incapacitating the target bacterium, with few or no side-effects to the eukaryotic host organism. As a result, inhibitors of TrxB activity are effective antimicrobial agents against Staphylococcus and other microorganisms that depend on TrxB for their redox reactions.

Accordingly, in one embodiment, the invention is directed to an isolated Staphylococcus TrxB polypeptide.

In another embodiment, the invention is directed to an isolated polynucleotide that encodes a Staphylococcus TrxB polypeptide.

In yet other embodiments, the invention is directed to a recombinant vector comprising the polynucleotide molecule, recombinant host cells transformed with the vector, and methods of producing recombinant polypeptides using the transformed cells.

In still a further embodiment, the invention is directed to an oligonucleotide probe capable of specifically hybridizing to a nucleic acid molecule encoding a Staphylococcus TrxB. The probe includes about 8 to about 50 contiguous nucleotides of the TrxB-encoding polynucleotide.

In still another embodiment of the invention, antibodies to a Staphylococcus TrxB polypeptide are provided.

In another embodiment, the invention is directed to a method of detecting the presence of Staphylococcus in a test sample suspected of containing a Staphylococcus, comprising:
 (a) contacting the test sample with the oligonucleotide probe above, under conditions which allow a Staphylococcus polynucleotide, when present in the test sample, to hybridize with the oligonucleotide probe to form a hybrid complex; and
 (b) detecting the presence or absence of the hybrid complex as an indication of the presence of a Staphylococcus in the test sample.

In yet another embodiment, the invention is directed to a method of detecting the presence of Staphylococcus in a test sample suspected of containing Stapylococcus, comprising:
 (a) contacting the test sample with a TrxB antibody, under conditions which allow a Staphylococcus TrxB, when present in the test sample, to bind to the antibody to form an antibody-TrxB complex; and
 (b) detecting the presence or absence of the antibody-TrxB complex, as an indication of the presence of Staphylococcus in the test sample.

In another embodiment, the invention is directed to a method of detecting a Staphylococcus in a test sample suspected of containing a Staphylococcus, comprising:
 (a) incubating the test sample with a disulfide-containing substrate in the presence of thioredoxin and NADPH, under conditions that favor reduction of the disulfide-containing substrate, to produce a detectable signal when a Staphylococcus thioredoxin reductase is present;
 (b) detecting the presence or absence of the signal; and
 (c) correlating the presence of the signal with the presence of Staphylococcus in the test sample.

In yet further embodiments, the invention is directed to diagnostic kits comprising an oligonucleotide probe as above, a TrxB antibody, or a Staphylococcus TrxB polypeptide, and instructions for conducting the diagnostic test.

In another embodiment, the invention is directed to a method for identifying a compound that modulates Staphylococcus TrxB activity, comprising:
 (a) providing a Staphylococcus TrxB polypeptide capable of catalyzing the specific reduction of thioredoxin with the concomitant oxidation of NADPH to $NADP^+$;
 (b) contacting a test compound with the TrxB polypeptide in the presence of thioredoxin, NADPH and a disulfide-containing substrate, under conditions that favor reduction of the disulfide-containing substrate;
 (c) monitoring the presence of free sulfhydryl groups formed by the reduction of disulfides of the disulfide-containing substrate, as a measure of TrxB activity, thereby identifying a compound that modulates Staphylococcus TrxB activity.

In yet further embodiments, the invention is directed to compounds identified by this method, compositions comprising the compounds and methods of treating Staphylococcus infections in an infected subject, comprising administering effective antibacterial amounts of the compositions.

In another embodiment, the invention is directed to a method for isolating a TrxB polypeptide from a Staphylococcus cell culture extract, comprising:
 (a) performing a protein precipitation step with the cell culture extract to yield a first TrxB mixture;
 (b) subjecting the first TrxB mixture to gel-filtration chromatography;
 (c) identifying fractions from step (b) with TrxB activity; and
 (d) performing anion-exchange chromatography on the fractions with TrxB activity to yield a product with a greater concentration of TrxB than the first TrxB mixture.

These and other embodiments of the present invention will readily occur to those of ordinary skill in the art in view of the disclosure herein.

BRIEF DESCRIPTION OF THE FIGURES

FIG. 1 depicts the nucleotide sequence (SEQ ID NO:1) of the S. aureus trxB open reading frame.

FIG. 2 shows the deduced amino acid sequence (SEQ ID NO:2) of S. aureus TrxB derived from the nucleotide sequence of the open reading frame.

FIG. 5A shows the construction of plasmid pOI4 used to construct plasmid pOI5, shown in FIG. 5B.

FIG. 6 depicts the nucleotide sequence (SEQ ID NO:9) of the S. epidermidis trxB open reading frame.

FIG. 7 shows an alignment of the TrxB enzymes from S. aureus (designated TrxB_Sa, SEQ ID NO:2) and S. epidermidis (designated TrxB_Se, SEQ ID NO:10). Colons indicate conservative amino acid substitutions and single dots indicate somewhat conservative substitutions.

DETAILED DESCRIPTION

Figure 3:
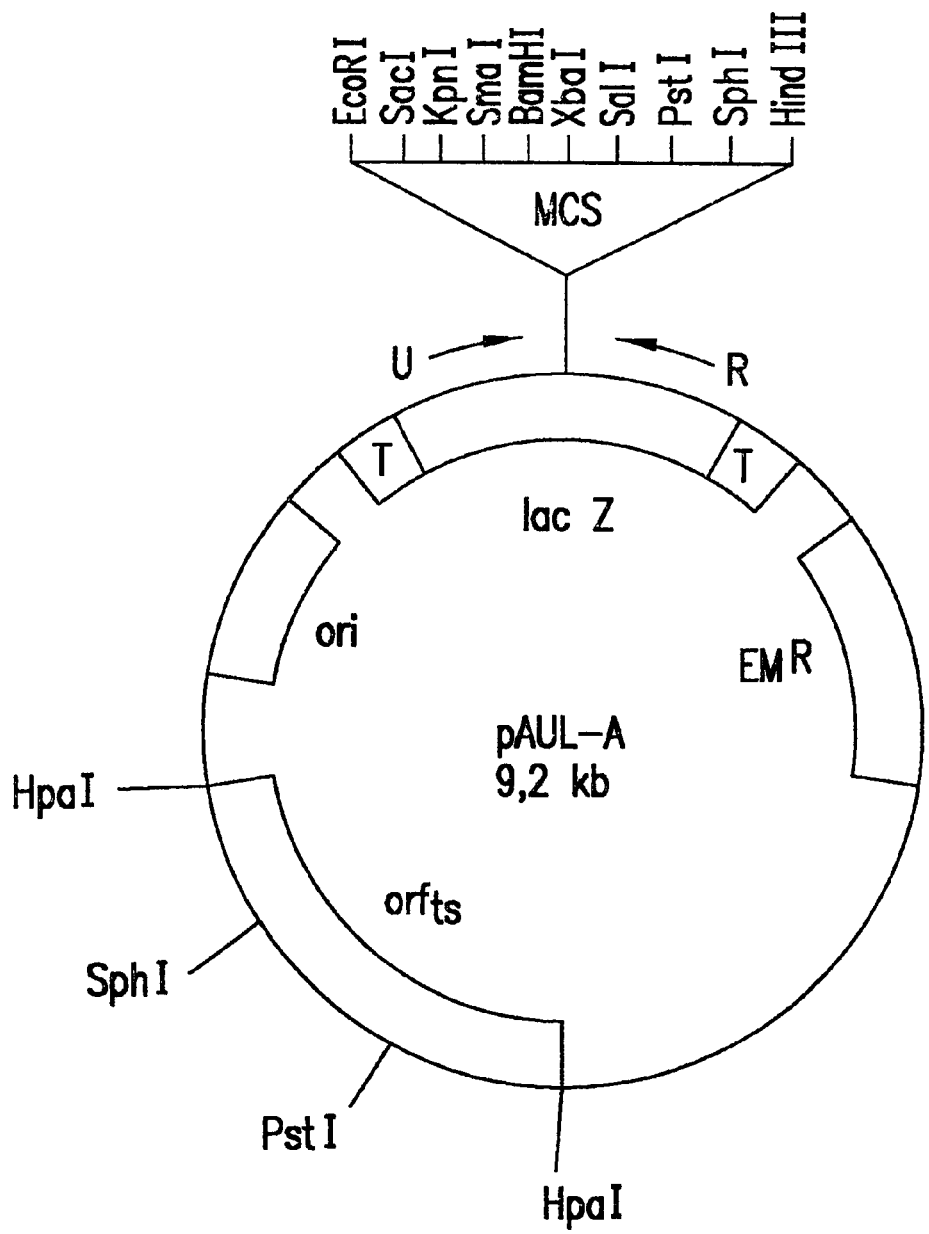
FIG. 3 is a diagram of vector pAUL-A.

The practice of the present invention will employ, unless otherwise indicated, conventional techniques of molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning, Vols*. I and II (D. N. Glover ed. 1985); the series, *Methods In Enzymology* (S. Colowick and N. Kaplan eds., Academic Press, Inc.); Scopes, *Protein Purification: Principles and Practice* (2nd ed., Springer-Verlag); and *PCR: A Practical Approach* (McPherson et al eds. (1991) IRL Press).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide.

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translation modifications of the polypeptide, for example, glycosylations, acetylations, phosphorylations, and the like. In addition, protein fragments, analogs, muteins, fusion proteins and the like are included within the meaning of polypeptide.

Thus, by "TrxB polypeptide" is meant a polypeptide, whether isolated, recombinant or synthetic, comprising an amino acid sequence identical to that depicted in FIG. 2 (SEQ ID NO:2) or 10 (SEQ ID NO:10), and fragments thereof that include as much of the molecule as necessary for the polypeptide to retain biological activity, e.g., catalytic and/or immunological activity, as well as analogs, mutated or variant proteins, and the like, thereof that retain such activity. Generally, if catalytic activity is required, the polypeptide will include the NADPH- and FAD-binding domains, as well as a redox active site. The NADPH domain is found at residues 146–161 of FIGS. 2 and 10. Two FAD domains are present, and found at residues 6–21 and 267–277, of FIGS. 2 and 10. Finally, the redox active site is found at residues 134–137 and includes the amino acid sequence CAVC. Thus, if catalytic activity is desired, the polypeptide can include about amino acid residues 1–277 or more of FIG. 2 or 10, or will include the above specified portions, with internal regions deleted, so long as catalytic activity is retained. If immunological activity is desired, e.g., the ability to raise antibodies for use in assays, immunopurification, and the like, the protein will contain one or more epitopes capable of eliciting a humoral antibody response. Normally, an epitope will include between about 3–20 amino acids, generally about 8–10, and preferably about 15–20 or more amino acids, derived from the TrxB molecule.

By sequence "similarity" between two amino acid sequences is meant an exact amino acid to amino acid comparison of two or more polypeptides at appropriate portions of the molecule, where identical amino acids are aligned, and where residues are not identical, aligned based on similar chemical and/or physical properties such as charge or hydrophobicity. "Percent similarity" can be determined between the compared polypeptide sequences using techniques well known in the art.

In general, "identity" refers to an exact nucleotide to nucleotide or amino acid to amino acid correspondence of two or more polynucleotide or polypeptide sequences, respectively. Techniques for determining nucleic acid and amino acid "sequence identity" are well known in the art and include determining the nucleotide sequence of the mRNA for the gene of interest (usually via a cDNA intermediate) and determining the amino acid sequence encoded thereby, and comparing this to a second amino acid sequence. Programs available in the Wisconsin Sequence Analysis Package, Version 8 (available from Genetics Computer Group, Madison, Wis.) for example, the GAP program, are capable of calculating both the identity between two polynucleotides and the identity and similarity between two polypeptide sequences. Other programs for calculating identity or similarity between sequences are known in the art.

Generally, a polypeptide analog of TrxB will have at least about 50% identity, preferably about 60% identity, more preferably about 75–85% identity, and most preferably about 90–95% or more identity, to the reference TrxB sequence. Further, the polypeptide may have at least about 60% similarity, preferably at least about 75% similarity, more preferably about 85% similarity, and most preferably about 95% or more similarity to the reference sequence. Additionally, a polynucleotide variant will display at least about 50% identity, preferably about 60% identity, more preferably about 75–85% identity, and most preferably about 90–95% or more identity, to the reference trxB nucleotide sequence.

By the term "degenerate variant" or "structurally conserved mutation" is intended a polynucleotide containing changes in the nucleic acid sequence thereof, such as insertions, deletions or substitutions, that encodes a polypeptide having the same amino acid sequence as the polypeptide encoded by the polynucleotide from which the degenerate variant is derived.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected.

A "vector" is a replicon in which another polynucleotide segment is attached, such as to bring about the replication and/or expression of the attached segment. The term includes expression vectors, cloning vectors, and the like.

The term "control sequence" refers to a polynucleotide sequence which effects the expression of coding sequences to which it is ligated. The nature of such a control sequence differs depending upon the host organism. In prokaryotes, such control sequences generally include a promoter, a ribosomal binding site, and a terminator. In eukaryotes, such control sequences generally include a promoter, a terminator and, in some instances, an enhancer. The term "control sequence" thus is intended to include at a minimum all components necessary for expression, and also may include additional components whose presence is advantageous, for example, leader sequences.

A "coding sequence" is a polynucleotide sequence that is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Mutants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell.

"Transformation" refers to the insertion of an exogenous polynucleotide into a host cell, irrespective of the method used for the insertion, or the molecular form of the polynucleotide that is inserted. For example, injection, direct uptake, transduction, and f-mating are included. Furthermore, the insertion of a polynucleotide per se and the insertion of a plasmid or vector comprised of the exogenous polynucleotide, are also included. The exogenous polynucleotide may be directly transcribed and translated by the cell, maintained as a nonintegrated vector, for example, a plasmid, or alternatively, may be stably integrated into the host genome.

The term "probe" denotes a defined nucleic acid segment which can be used to identify a specific polynucleotide present in samples bearing the complementary sequence. A probe will generally include about 8 to about 75 contiguous nucleic acids of the reference polynucleotide, generally about 12 to about 50 contiguous nucleic acids, and preferably about 15–18 to about 30 contiguous nucleic acids of the reference sequence.

The term "isolated," when referring to a polynucleotide or a polypeptide, intends that the indicated molecule is present in the substantial absence of other similar biological macromolecules of the same type. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include conservative mutations as defined herein. Thus, an isolated polynucleotide would not be a polynucleotide as it exists on the chromosome.

The term "test sample" refers to a component of an individual's body which is the source of an analyte, such as antibodies or antigens of interest. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

The following single-letter amino acid abbreviations are used throughout the text:

| Alanine | A | Arginine | R |
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

B. General Methods

The present invention is based on the identification of novel Staphylococcal TrxB polypeptides, including *S. aureus* TrxB (also termed TrxB_Sa herein) and *S. epidermidis* TrxB (also termed TrxB_Se herein), as well as polynucleotides encoding the TrxBs, and methods of making the TrxBs. The invention includes not only the enzyme but also methods for screening compounds for pharmacological activity using the enzyme, cells expressing the enzyme, antibodies to the enzyme and the use of polynucleotides and antibodies to diagnose the presence of Staphylococcus in a test sample.

In particular, the inventors herein have identified new TrxB enzymes in *S. aureus* and *S. epidermidis*. The native enzyme has a molecular mass ($M_r$) of approximately 70 kDa, as determined by gel filtration chromatography. The enzyme exists as a homodimer having a subunit $M_r$ of about 35 kDa, as determined by SDS polyacrylamide gel electrophoresis. The predicted value of the Staphylococcal TrxB subunit molecular mass, based on the primary amino acid sequence is 33.518, and the calculated isoelectric point (PI) is 5.39. The gene encoding the *S. aureus* TrxB enzyme has been cloned and the ORF coding for the TrxB protein is shown in FIG. 1. The gene encodes a putative amino acid sequence of 311 amino acids, shown in FIG. 2.

Similarly, the gene encoding the *S. epidermidis* TrxB enzyme has been identified and the nucleotide and amino acid sequences are shown in FIGS. 6 and 7, respectively.

The enzyme can be isolated directly from bacteria as follows. Bacteria are cultured in a suitable culture medium, such as trypticase soy broth (TSB). The bacteria are then removed from the culture medium using standard techniques known in the art, such as by centrifugation or microfiltration or a combination of the two. For example, microfiltration using an appropriate filter will suffice to remove unwanted cellular debris.

Bacteria thus obtained are prepared to release the contents of the cytoplasm. Bacterial cells may be broken using methods and/or reagents known in the art that do not adversely affect the structure and/or the activity of the TrxB, e.g., exposure to freeze-thaw cycles, exposure to an ultrasonic disintegrator, homogenization, bead milling, chemical or enzymatic cell lysis, and the like. In one preferred method, cells are incubated in a buffer containing lysostaphin, a lytic agent for S. aureus, and then centrifuged to remove insoluble cellular debris.

The bacterial cell extract thus prepared can be further processed to separate the protein from the cellular debris, and provide an initial stage of purification and volume reduction. For example, the extract obtained from the previous step may be processed by a primary separation procedure such as ultrafiltration, i.e., passage through a filter having an appropriate molecular weight cut-off, to concentrate the sample by reducing the water and salt content. Alternatively, the extract may be precipitated by neutral salts such as ammonium sulphate, organic solvents such as ethanol, or other agents for recovering and purifying the protein. Preferably, Staphylococcus TrxB is precipitated from the extract by adding ammonium sulfate to the extract to approximately 30% to 50% saturation, preferably 40% saturation. The supernatant of the same is collected by, e.g., centrifugation, and the ammonium sulfate is adjusted to about 70% to 90%, preferably 80% saturation. The treated precipitate thus obtained is collected and used in further purification steps.

A number of protein purification operations may be used to further purify the Staphylococcus TrxB including adsorption chromatography, ion-exchange chromatography, hydrophobic interaction chromatography, affinity chromatography, chromatofocussing, gel-filtration, reversed-phase liquid chromatography, phosphocellulose chromatography, hydroxyapatite chromatography or lectin chromatography, any combination of such techniques. Protein refolding steps can be used, as necessary, in completing configuration of the protein. Finally, high performance liquid chromatography (HPLC) can be employed for final purification steps.

For example, the fraction precipitating between 40–80% ammonium sulfate saturation can be applied to a gel-filtration matrix for size separation. Useful matrices for size separation include any of several known in the art such as, without limitation, those made of dextran, dextran/bisacrylamide, polyacrylamide, agarose, cross-linked agarose, agarose/polyacrylamide, and cross-linked polyethers. Particularly preferred matrices are those which allow fractionation of molecules in the size range of about $10^4$ to $10^6$, such as Sephacryl S-300, Sepharose 6B, Sepharose CL-6B, Ultragel AcA44, Ultragel AcA34, Ultragel A6, and the like.

Fractions from the size-separation step which exhibit TrxB and Trx activity can be pooled and applied to an ion-exchange column and proteins eluted with a linear salt gradient. Preferred ion-exchangers are anion-exchangers, well known in the art. Particularly preferred herein are relatively weak anion-exchangers, such as those including aminoethyl (AE) or diethylaminoethyl (DEAE) functionalities. Useful matrix materials include but are not limited to, cellulose matrices, such as fibrous, icrogranular and beaded matrices; agarose, dextran, polyacrylate, polyvinyl, polystyrene, silica and polyether matrices; and composites. A representative anion-exchanger for use herein is DEAE-Sepharose.

TrxB activity can be monitored during purification using standard TrxB assays. For example, the presence of TrxB can be assayed spectrophotometrically by monitoring the NADPH- and TrxB disulfide-dependent reduction of a disulfide-containing substrate. One assay method monitors the reduction of 5,5'-dithio-bis-2-nitrobenzoic acid (DTNB) at 412 nm. See, e.g., Ellman (1959) *Arch. Biochem. Biophys.* 82:70–77. A particularly preferred assay uses insulin as the disulfide-containing substrate. The presence of free sulfhydryl (SH) groups in insulin are measured at 650 nm as an indication of TrxB activity. See, e.g., A. Holmgren and M. Bjornstedt, (1995) *Methods in Enzymology* 252:199–208; and the examples herein. In this reaction, TrxB specifically reduces thioredoxin (T-$S_2$) to T-$(SH)_2$ using NADPH. The formed T-$(SH)_2$ in turn reduces native insulin. Insulin can be replaced by any of several low molecular weight disulfide compounds in the assay, such as cystine, and TrxB activity is monitored spectrophotometrically following the oxidation of NADPH.

Following isolation, purity of fractions showing TrxB activity can be determined using any of several methods such as by SDS-PAGE.

Once purified, the amino acid sequences of the proteins can be determined, e.g., by repetitive cycles of Edman degradation, followed by amino acid analysis by HPLC. Other methods of amino acid sequencing are also known in the art. Based on knowledge of the amino acid sequence, DNA encoding the enzyme can be derived from genomic or cDNA, prepared by synthesis, or by a combination of techniques. The DNA can then be used to express the TrxB, or as a template for the preparation of RNA, using methods well known in the art (see, Sambrook et al., supra).

More particularly, DNA encoding the Staphylococcus TrxB may be obtained from an appropriate DNA library, e.g., an S. aureus or S. epidermidis genorhic DNA library. DNA libraries may be probed using the procedure described by Grunstein et al. (1975) *Proc. Natl. Acad. Sci. USA* 73:3961. Briefly, the DNA to be probed is immobilized on nitrocellulose filters, denatured and prehybridized with a buffer which contains 0–50% formamide, 0.75 M NaCl, 75 mM Na citrate, 0.02% (w/v) each of bovine serum albumin (BSA), polyvinyl pyrollidone and FicoII®, 50 mM Na phosphate (pH 6.5), 0.1% sodium dodecyl sulfate (SDS) and 100 μg/ml carrier denatured DNA. The percentage of formamide in the buffer, as well as the time and temperature conditions of the prehybridization and subsequent hybridization steps, depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, for example, about 40° C. to 42° C., and a high percentage, for example, 50%, formamide. Following prehybridization, a $^{32}$P-labelled oligonucleotide probe is added to the buffer, and the filters are incubated in this mixture under hybridization conditions. After washing, the treated filters are subjected to autoradiography to show the location of the hybridized probe. DNA in corresponding locations on the original agar plates is used as the source of the desired DNA.

Synthetic oligonucleotides may be prepared using an automated oligonucleotide synthesizer such as that described by Warner (1984) *DNA* 3:401. If desired, the synthetic strands may be labeled with $^{32}$P by treatment with polynucleotide kinase in the presence of $^{32}$P-ATP, using standard conditions for the reaction. DNA sequences including those isolated from genomic or cDNA libraries, may be modified by known methods which include site-directed mutagenesis as described by Zoller (1982) *Nucleic Acids Res.* 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned.

Once produced, the DNA may then be incorporated into a cloning or expression vector for replication in a suitable host cell. Vector construction employs methods known in the art. Generally, site-specific DNA cleavage is performed by treating with suitable restriction enzymes under conditions which generally are specified by the manufacturer of these commercially available enzymes. Usually, about 1 microgram ($\mu$g) of plasmid or DNA sequence is cleaved by 1–10 units of enzyme in about 20 $\mu$l of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Sticky-end ligations require less ATP and less ligase than blunt-end ligations. When vector fragments are used as part of a ligation mixture, the vector fragment often is treated with bacterial alkaline phosphatase (BAP) or calf intestinal alkaline phosphatase to remove the 5'-phosphate and thus prevent religation of the vector. Alternatively, restriction enzyme digestion of unwanted fragments can be used to prevent ligation.

For standard vector constructions, ligation mixtures are transformed into a suitable host, and successful transformants selected by antibiotic resistance or other markers. Plasmids from the transformants can then be prepared according to the method of Clewell et al. (1969) *Proc. Natl. Aced. Sci. USA* 62:1159 usually following chloramphenicol amplification as reported by Clewell et al. (1972) *J. Bacteriol.* 110:667. The DNA is isolated and analyzed usually by restriction enzyme analysis and/or sequencing. Sequencing may be by the well-known dideoxy method of Sanger et al. (1977) *Proc. Natl. Aced. Sci. USA* 74:5463) as further described by Messing et al. (1981) *Nucleic Acid Res.* 9:309, or by the method reported by Maxam et al. (1980) *Meth. Enzymol.* 65:499. Problems with band compression, which are sometimes observed in GC rich regions, are overcome by use of T-deazoguanosine according to the method reported by Barr et al. (1986) *Biotechniques* 4:428.

Host cells are genetically engineered (transduced, transformed, or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying the TrxB-encoding polynucleotide. The culture conditions, such as temperature, pH and the like, are those previously used with the host cell selected for expression, and will be apparent to those of skill in the art.

Both prokaryotic and eukaryotic host cells may be used for expression of desired coding sequences when appropriate control sequences that are compatible with the designated host are used. Among prokaryotic hosts, *E. coli* is frequently used. Expression control sequences for prokaryotes include promoters, optionally containing operator portions, and ribosome binding sites. Transfer vectors compatible with prokaryotic hosts are commonly derived from the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include the $\beta$-lactamase (penicillinase), lactose promoter system (Chang et al. (1977) *Nature* 198:1056), the tryptophan promoter system (reported by Goeddel et al. (1980) *Nucleic Acid Res.* 8:4057) and the lambda-derived PI promoter and N gene ribosome binding site (Shimatake et al. (1981) *Nature* 292:128) and the hybrid Tac promoter (De Boer et al. (1983) *Proc. Natl. Acad. Sci. USA* 292:128) derived from sequences of the trp and lac UV5 promoters. The foregoing systems are particularly compatible with *E. coli*; however, other prokaryotic hosts such as strains of Bacillus or Pseudomonas may be used if desired, with corresponding control sequences.

Eukaryotic hosts include yeast and mammalian cells in culture systems. *Saccharomyces cerevisiae* and *S. carlsbergensis* are commonly used yeast hosts, and are convenient fungal hosts. Yeast-compatible vectors carry markers that permit selection of successful transformants by conferring protrophy to auxotrophic mutants or resistance to heavy metals on wild-type strains. Yeast compatible vectors may employ the 2-micron origin of replication (Broach et al. (1983) *Meth. Enzymol.* 101:307), the combination of CEN3 and ARS1 or other means for assuring replication, such as sequences that will result in incorporation of an appropriate fragment into the host cell genome. Control sequences for yeast vectors are known in the art and include promoters for the synthesis of glycolytic enzymes, including the promoter for 3-phosphoglycerate kinase. See, for example, Hess et al. (1968) *J. Adv. Enzyme Reg.* 7:149, Holland et al. (1978) *Biochemistry* 17:4900, and Hitzeman (1980) *J. Biol. Chem.* 255:2073. Terminators also may be included, such as those derived from the enolase gene as reported by Holland (1981) *J. Biol. Chem.* 256:1385. It is contemplated that particularly useful control systems are those that comprise the glyceraldehyde-3-phosphate dehydrogenase (GAPDH) promoter or alcohol dehydrogenase (ADH) regulatable promoter, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines which are available from the American Type Culture Collection. These include HeLa cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV), cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which insure integration of the appropriate sequences encoding the Staphylococcus TrxB into the host genome.

Other eukaryotic systems are also known, as are methods for introducing polynucleotides into such systems, such as into amphibian cells, using known methods, and insect cells using methods described in Summers and Smith (1987), *Texas Agricultural Experiment Station Bulletin No.* 1555, and the like.

Transformation may be by any known method for introducing polynucleotides into a host cell, including packaging the polynucleotide in a virus and transducing a host cell with the virus, by direct uptake of the polynucleotide by the host cell, and the like. The transformation procedures selected depend upon the host to be transformed. Bacterial transformation by direct uptake generally employs treatment with calcium or rubidium chloride. Cohen (1972) *Proc. Natl. Acad. Sci. USA* 69:2110. Yeast transformation by direct uptake may be conducted using the calcium phosphate precipitation method of Graham et al. (1978) *Virology* 52:526, or modification thereof.

Expression of active TrxB can be assayed spectrophotometrically, as described above, by monitoring the NADPH- and TrxB disulfide-dependent reduction of a disulfide-containing substrate. Particularly useful substrates include DTNB and insulin. See, e.g., Ellman (1959) *Arch. Biochem. Biophys.* 82:70–77; and A. Holmgren and M. Bjornstedt, (1995) *Methods in Enzymology* 252:199–208. Alternatively, expression of TrxB can be monitored using an ELISA assay and antibodies prepared to the isolated TrxB enzyme. The enzyme is recovered and purified from recombinant host cell cultures expressing the same by known methods as described above.

The Staphylococcus TrxB polypeptide or fragments thereof, may also be synthesized by conventional techniques known in the art, for example, by chemical synthesis such as solid-phase peptide synthesis. In general, these methods employ either solid- or solution- phase synthesis methods, well known in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Once obtained, the enzyme may be used to identify compounds that modulate Staphylococcus TrxB activity. Thus, as described above, enzyme activity and the effects of compounds on enzyme activity can be assayed spectrophotometrically by monitoring the NADPH- and TrxB disulfide-dependent reduction of 5,5'-dithio-bis-2-nitrobenzoic acid (DTNB) at 412 nm, or by measuring the presence of free SH groups of insulin at 650 nm.

Purification or expression of Staphylococcus TrxB, and screening for compounds that inhibit the enzyme activity, provides a method for rapid selection of compounds with enzyme-inhibiting activity.

Compounds that inhibit Staphylococcus TrxB are considered potential therapeutic agents for use in treating several disorders caused by staphylococcal bacteria, including without limitation those caused by *S. aureus, S. epidermidis, S. albus, S. hyicus, S. hyos, S. intermedius, S. simulans*, and the like. These bacteria cause infection in man and other non-human primates, as well as in domestic animals, such as dogs and cats, and in farm animals, including horses, pigs, sheep, goats and cows. These agents are therefore useful in preventing or retarding growth and/or reproduction of the infecting microorganism in a wide variety of vertebrate subjects.

Examples of diseases for which TrxB inhibitors are useful therapeutic agents include any of the several infections caused by staphylococci including, but not limited to, gastroenteritis, enterocolitis, toxic shock syndrome, scalded skin syndrome, dermal infections, cellulitis, toxic epidermal necrolysis, ecthyma, necrotizing fasciitis, folliculitis, furuncles, carbuncles, impetigo, bone and joint infections, osteomyelitis, pneumonia and empyema, meningitis, cerebritis, endocarditis, bacteremia, septic shock, septicemia, food poisoning, enteritis, and the like.

The inhibitory compounds of the present invention can be formulated into pharmaceutical compositions in a variety of dosage forms such as, but not limited to, liquid solutions or suspensions, tablets, pills, powders, ointments suppositories, polymeric microcapsules or microvesicles, liposomes, and injectable or infusible solutions. The preferred form depends upon the mode of administration and the particular microorganism and disease targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intramuscular, intravenous, intraperitoneal, oral, intralymphatic, or subcutaneous administration. Local administration to a tissue in question, or to a site of infection, e.g., direct injection into an infected joint, will also find use with the present invention.

Therapeutically effective doses will be easily determined by one of skill in the art and will depend on the severity and course of the disease, the patient's health and response to treatment, and the judgment of the treating physician.

Furthermore, the Staphylococcus TrxB polypeptide can be used to prepare polyclonal or monoclonal antibodies using techniques that are well known in the art. If polyclonal antibodies are desired, a selected mammal, (e.g., mouse, rabbit, goat, horse, etc.) is immunized with a TrxB polypeptide and serum from the immunized animal is collected and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies to the TrxB polypeptides can also be readily produced by one skilled in the art. The general methodology for making monoclonal antibodies using hybridoma technology is well known. Immortal antibody-producing cell lines can be created by cell fusion, as well as by other techniques, such as direct transformation of B-lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); U.S. Pat. Nos. 4,341,761; 4,399, 121; 4,427,783; 4,444,887; 4,452,570; 4,466,917; 4,472, 500, 4,491,632; and 4,493,890. Panels of monoclonal antibodies produced against the TrxB polypeptides can be screened for various properties; e.g., for isotype, epitope, affinity, etc. Monoclonal antibodies are useful in purification, using immunoaffinity techniques, of the TrxB polypeptides. Monoclonal and polyclonal antibodies that display specificity and selectivity for the enzyme can be labeled with a detectable moiety, e.g., a fluorescent moiety, and used in in vitro, or in situ immunofluorescent assays, or the like. The antibodies can be used to identify Staphylococcus for immunodiagnostic purposes.

In addition, DNA encoding the Staphylococcus TrxBs, or RNA derived therefrom, can be used to design oligonucleotide probes for Staphylococcus present in a host organism. As used herein, the term "probe" refers to a structure comprised of a polynucleotide, as defined above, which contains a nucleic acid sequence complementary to a nucleic acid sequence present in a target polynucleotide. The polynucleotide regions of probes may be composed of DNA, and/or RNA, and/or synthetic nucleotide analogs such as morpholino compounds and peptide nucleic acid ("PNA") analogs. Such probes may be used in in vitro or in situ hybridization assays, or the like, and are useful, for example, for the diagnosis of microbial infections.

Using a determined portion of the isolated TrxB-encoding polynucleotide, oligomers of approximately eight or more nucleotides can be prepared, either by excision or synthetically, which hybridize with the TrxB-encoding polynucleotide. Such oligomers are useful, for example, for detecting the presence of bacteria in diseased individuals. The natural or derived probes for trxB polynucleotides are a length that allows the detection of unique sequences by hybridization. While 6–8 nucleotides may be a workable length, sequences of 10–12 nucleotides are preferred, and those of about 18–20 nucleotides, or more, most preferred. These probes can be prepared using routine, standard methods including automated oligonucleotide synthetic methods.

When the oligonucleotide probes are to be used as diagnostic reagents, the test sample to be analyzed, such as blood or serum, may be treated such as to extract a nucleic acid fraction thereof. The resulting nucleic acid from the sample may be subjected to gel electrophoresis or other size separation techniques, or the nucleic acid sample may be dot-blotted without size separation. The sample is then exposed to an oligonucleotide probe that has been detectably labeled. Suitable labels and methods for attaching labels to probes are known in the art, and include but are not limited to radioactive labels incorporated by nick translation or kinasing, biotin, fluorescent and chemiluminescent probes, enzymes which catalyze the production of a detectable product such as horseradish peroxidase, alkaline phosphatase, β-galactosidase, and the like. The nucleic acids extracted from the sample are then treated with the labeled probe under conditions of suitable hybridization stringency.

The stringency of hybridization is determined by a number of factors during the washing procedure, including temperature, ionic strength, length of time and concentration of formamide. Sambrook et al., supra. Hybridization can be carried out by a number of techniques. Amplification of the sample nucleic acid, if required, can be performed, for example, by ligase chain reaction (LCR), polymerase chain reaction (PCR), Q-beta replicase, NASBA, or other techniques well known in the art. The amplified nucleic acids then may be detected using a hybridization assay such as those known in the art.

TrxB, antibodies thereto, as well as polynucleotides encoding TrxB or portions thereof, can be provided in diagnostic kits. For example, oligomer probes capable of specifically hybridizing to a polynucleotide encoding a TrxB can be packaged in diagnostic kits which include the probe nucleic acid sequence which may be labelled. Alternatively, the probe may be provided unlabelled and the ingredients for labelling can be included with the kit. The kit also may contain other suitably packaged reagents and materials needed or desirable for the particular hybridization protocol, for example, standards as well as instructions for performing the assay.

In addition, kits can include reagents for detecting of the presence and/or amount of Staphylococcus TrxB in a test sample, as well as for detecting the presence of Staphylococcus. Such reagents can comprise, e.g., an antibody capable of specifically binding to the TrxB polypeptide.

Furthermore, kits containing a Staphylococcus TrxB polypeptide in a suitable container are provided for screening compounds for TrxB-modulating activity or for screening test samples for the presence of a TrxB antibody. It is contemplated that. reagents employed in the above kits can be provided in one or more containers such as vials or bottles, with each container containing a separate reagent such as a monoclonal antibody, or a cocktail of monoclonal antibodies, or a polypeptide (either recombinant or synthetic) employed in the assay. Other components such as buffers, controls, and the like, known to those of ordinary skill in art, may be included in such test kits. The kits will also include instructions for the use thereof.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

C. Experimental

EXAMPLE 1

Identification of a Thioredoxin Reductase from *S. aureus*

In order to identify the enzyme responsible for the reduction of oxidized thioredoxin (Trx), *S. aureus* extracts were analyzed for thioredoxin reductase (TrxB) activity on oxidized thioredoxin in a NADPH-dependent reaction specific for the reduction of insulin as the protein disulfide substrate. 10 ml of an overnight culture of *S. aureus* RN8325-4 (obtained from Richard Novick at New York University School of Medicine), grown at 37° C. in tryptic soy broth (TSB) medium (Difco Laboratories, Detroit, Mich.), was used to inoculate 0.5 L fresh sterilized TSB medium and the culture was grown for 4 hours. Cells were harvested by centrifugation (8000×g, 15 min), resuspended in 50 mM Tris HCl buffer (20 ml) containing 1 mM EDTA and disrupted by sonication. The homogenized suspension was cleared from insoluble cellular debris by centrifugation and saved. The supernatant was brought to a final concentration of 1% streptomycin sulfate, stirred for 30 min and the nucleic acid precipitate removed by centrifugation. Ammonium sulfate was added to the clear liquid and the fraction that precipitated between 40–80% ammonium sulfate saturation was collected by centrifugation, dissolved in a minimal volume of buffer and chromatographed on a AcA44 gel-filtration size column.

Fractions exhibiting TrxB activity were separated from those containing the Trx activity and served as the high and low molecular weight protein components, respectively, in the thioredoxin assay. High molecular weight protein fractions were added to a reaction mixture containing an excess of Trx, NADPH and insulin, and the formation of free sulfhydryl (SH) groups in insulin was detected by titration with 5,5'-dithio-bis-2-nitrobenzoic acid (DTNB), which forms a yellow product (TNB, absorbance maximum at 412 nm) on interaction with free thiols. The reduction of the insulin disulfides is strictly dependent on the presence of each of reaction components (NADPH, TrxB, Trx). DTNB may be used in place of insulin as the substrate for the Trx-driven reaction, but is less specific. See, e.g., Ellman (1959) *Arch. Biochem. Biophys.* 82:70–77.

A typical assay (Table 1) consisted of a 40 μl fraction of the high molecular weight component from the AcA44 gel-filtration column to which was added 40 μl of a solution containing HEPES buffer pH 7.6, 0.26 M; EDTA 0.01 M; NADPH 2.0 mM; insulin, 1.03 mM. The reaction was initiated by adding a 20 μl fraction of the low molecular weight Trx component eluted from the same gel-filtration column and the mixture was incubated for 20 min at 37° C. The reaction was stopped with 500 μl of a solution containing 0.4 mg DTNB/ml and 6 M Guanidine HCl in 0.2 M Tris HCl, pH 8.0, and the absorbance $A_{412}$ read. Table 1 shows the ability of the *S. aureus* thioredoxin system to reduce insulin disulfides in the presence of NADPH.

TABLE 1

Identification of thioredoxin reductase activity in *Staphylococcus aureus*

| Reaction/Components | NADPH | Trx[a] | TrxB | Insulin | $A_{412}$ |
|---|---|---|---|---|---|
| Trx | + | − | + | + | 0.493 |
| NADPH | − | + | + | + | 0.150 |
| Complete | + | + | + | + | 0.816 |

[a]The $A_{412}$ reading observed when Trx is omitted in the assay, reflects presence of some Trx and other thiols in the partially purified TrxB preparation employed.

EXAMPLE 2

Purification and Characterization of a Thioredoxin Reductase from *S. aureus*

TrxB was purified from cell extracts of *S. aureus* by following the NADPH-dependent reduction of DTNB. An overnight culture of *S. aureus* strain RN8325-4 grown in TSB (100 ml) at 37° C. was used as inoculum (5%) for each of two 2 L flasks containing TSB (0.5 L). Cells were shaken (200 rpm) for 4 hrs at 37° C. before being harvested by centrifugation (Sorvall GSA rotor, 5000 rpm, 15 min). All subsequent handling of the sample prior to chromatography was carried out at 4° C. The cell pellet was resuspended in a minimum of TE buffer (50 mM Tris HCl, pH 8.0, 1 mM EDTA) containing phenylmethylsulphonyl fluoride (PMSF) (1 mM) and lysostaphin (0.5 mg), incubated at 4° C., stirred for 30 min, disrupted further by sonication and then centrifuged (15,000×g, 20 min) to remove insoluble cellular debris. Streptomycin was added to a final concentration of 1%, stirred for 30 min at 4° C. and the nucleic acid precipitate removed by centrifugation. The clear supernatant was brought to 40% saturation with ammonium sulfate, stirred to 15 min, and centrifuged (15,000×g, 10 min). The resulting supernatant was adjusted to 80% saturation with ammonium sulfate and the precipitate collected by centrifugation. The fraction precipitating between 40–80% ammonium sulfate saturation was dissolved in a small volume of buffer and applied to an AcA44 gel-filtration column for size separation chromatography.

Fractions containing the TrxB activity were easily separated from those containing the Trx activity. Fractions exhibiting TrxB and Trx activity were pooled, dialyzed and applied to a DEAE-Sepharose ion exchange column. The column was washed with the loading buffer (TE) and eluted with a linear gradient of NaCl (0.0–0.5 M) in TE buffer. Fractions containing the TrxB activity were collected and used for further reactions. The purity of fractions showing TrxB activity was determined by SDS-PAGE. The molecular weight of the monomer was determined to be approximately 35 kDa using SDS-PAGE.

EXAMPLE 3

Cloning of the Gene Encodinq *S. aureus* TrxB

The gene encoding *S. aureus* TrxB (trxB_Sa) was isolated and sequenced as described below. Generally, the gene was identified by PCR using degenerate primers, shown in Table 2A, based on the conserved N-terminal and C-terminal sequences, shown in Table 2B, of known bacterial thioredoxin reductases. See, e.g., Russell et al. (1988) *J. Biol. Chem.* 263:9015–9019, for the sequence of *E. coli* TrxB; Cohen et al. (1993) *J. Bacteriol.* 175:5159–5167, for the sequence of *S. clavuligerus* TrxB; Cohen et al. (1994) *J. Bacteriol.* 176:973–984, for the sequence of Penicillium chrysogenum TrxB; Dai et al. (1996) *J. Mol. Biol.* 264:1044–1057, for the sequence of *Arabidopsis thaliana* TrxB; Lubbers et al. (1993) i Eur. J. Biochem. 217:791–798, for the sequence of *Eubacterium acidominophilum* TrxB; and Chae et al. (1994) *J. Biol. Chem.* 269:27670–27678, for the sequence of *Saccharomyces cerevisiae* TrxB. The DNA fragment generated by PCR was labeled and used as a probe in the isolation of a 2.8 kB XbaI fragment from *S. aureus* genomic DNA that carried the trxB gene. The sequence of the open reading frame and the deduced amino acid sequence are shown in FIG. 1 (SEQ ID NO:1) and FIG. 2 (SEQ ID NO:2), respectively.

TABLE 2A

Degenerate Oligodeoxynucleotide Primers Used in the PCR
Amplification of an Internal Region of the Gene Encoding TrxB

| Oligomer | Sequence[a] |
|---|---|
| P1 5'-ACIACIGAIGTIGA(AG)AA(CT)U(CT)CC(AGCT)GG-3'<br>(N-terminal region) | (SEQ ID NO:3) |
| M6 5'-ACGTCICCIGCIGC(AG)AA(AGCT)AC(AGCT)CC-3'<br>(C-terminal region) | (SEQ ID NO:4) |

[a]I denotes inosine.

TABLE 2B

Peptide Regions Specified by Degenerate
Oligonucleotide Primers Used in PCR Amplification
of an Internal Segment of the Gene Encoding TrxB

| Region | Sequence |
|---|---|
| N-terminal peptide | TEEVENFPG (SEQ ID NO:5) |
| C-terminal peptide | GIFAAGD (SEQ ID NO:6) |

A. Isolation of a Large Internal DNA Fragment of the trxB Gene

Degenerate oligodeoxynucleotides which were designed to encode the N-terminal and C-terminal trxB sequences were used as primers for PCR of S. aureus genomic DNA. The PCR reaction contained the following:

100 ng genomic DNA, 50 μm each of
5'-ACIACIGAIGTIGA(AG)M(CT)TT(CT)CC(AGCT)GG-3' (SEQ ID NO:3) and
5'-ACGTCICCIGCIGC(AG)AA(AGCT)AC(AGCT)CC-3' (SEQ ID NO:4); $MgCl_2$ (1.5 mM); bovine serum albumin (BSA) (5 μg); deoxynucleotide triphosphates (dNTPs) (0.2 mM each); and 1×PCR buffer (Fermentas, MBI). The reaction mixture was incubated at 94° C. (1 min), 55° C. (2 min) and 72° C. (2 min) for 30 cycles. The resulting 700 bp PCR product was cloned directly using an AT cloning kit (Promega) and sequenced using universal "forward" and "reverse" primers which are homologous to the flanking region of the multiple cloning site within the plasmid pGEMT (the AT cloning vector (Promega)). The cloning vector including the 700 bp PCR product was termed pOI1.

B. Cloning and Sequencing of the Gene Encoding TrxB

The fragment from above was labeled with digoxygenin and used to probe Southern blots of S. aureus genomic DNA digested with various restriction enzymes. A single 2.8 kb XbaI fragment that hybridized to the probe under stringent conditions (50% formamide, 42 C) was subcloned into plasmid pUC18 to form pOI2 and sequenced. Initial sequencing primers were designed to prime within the sequence of the PCR fragment described above and to sequence into the flanking regions. New primers were designed within the new sequences and the nucleotide sequence of the entire gene was thus determined stepwise. All of the sequences were confirmed by sequencing both the coding and non-coding strands.

C. Sequence Analysis of S. aureus trxB

The sequence of the S. aureus trxB gene and the deduced amino acid sequence are shown in FIG. 1 (SEQ ID NO:1) and FIG. 2 (SEQ ID NO:2), respectively. Using the CLUST-ALW Program (Thompson et al. (1994) Nucl. Acid Res. 22:46734680), the S. aureus TrxB amino acid sequence was compared to other bacterial TrxBs. All parameters used were the standard default parameters recommended by CLUST-ALW (see, web site http://www2.ebi.ac.uk/clustalw). Sequence identities found were Bacillus subtilis (72%), Listeria monocytogenes (65%), Clostridium litorale (53%), Mycobacterium leprae (45.5%), Streptomyces coelicolor (43.7%), Escherichia coli (41.9%), Mycoplasma genitalis (35%).

D. Heterologous Overexpression of S. aureus trxB in E. coli

The open reading frame encoding S. aureus TrxB is amplified by the PCR reaction using the N-terminal primer 5'-GGGAATTCCATATGACTGAAATAGATTTTGAT-3' (SEQ ID NO:7) and the C-terminal PCR primer 5'-CCCAAGCTTTTAAGCTTGATCGTTTAA-3' (SEQ ID NO:8). The resulting fragment is digested with NdeI and HindIII, purified and ligated with vector pET14b (Novagen, Inc. Madison Wis.) that is digested with the same two enzymes and purified similarly to produce plasmid pTRSA. An overnight culture (10 mL) of E. coli BL21 (DE3) cells harboring PTRSA is washed twice in 10 ml of TB medium and used as an inoculum for 1 liter of the same medium containing ampicillin (400 mg/mL). The resulting culture is incubated at 37° C. until it reaches mid-stationary phase ($A_{600} \approx 1.2$), induced to express recombinant TrxB (rTrxB) by the addition of IPTG (to 1 mM) and then incubated for an additional 3 hours at 37° C. The cells are harvested and the recombinant enzyme is purified as described in Example 2 for native TrxB, except that lysozyme (2 mg/mL) is used in place of lysostaphin to assist in disrupting the cells. The purity of the resulting recombinant enzyme is measured by SDS-PAGE and staining with Coomasie brilliant blue.

E. Construction of Gene Replacement Shuttle Vector

Plasmid pAUL-A (Chakraborty et al. (1992) J. Bacteriol. 174:568–574; FIG. 3), used for trxB inactivation in S. aureus and S. epidermidis, contains a temperature sensitive origin of replication for Staphylococcus such that, when the temperature is raised to 42° C., the plasmid cannot replicate. Additionally, the plasmid contains the origin of replication of pBR322 and is therefore able to propagate in both E. coli and in the above bacteria. If the inactivation plasmid carries a segment of the host chromosome, recombination between the homologous segments will result in the integration of the plasmid. At 42° C., the integrated plasmid can be stably maintained employing selection for the genetic marker, erythromycin resistance, carried on the plasmid sequence. If the homologous chromosomal fragment represents a segment internal to a gene, a single recombinational crossover of the plasmid into the chromosome will cause disruption of the gene and result in the inactivation of the corresponding polypeptide. If the homologous chromosomal fragment contains a deletion internal to a gene, a single recombinational crossover of the plasmid into the chromosome generates a tandem arrangement of wild-type and mutant genes separated by the plasmid sequence; a second recombination event results in loss of one of the copies and the intervening plasmid sequence which, if of the wild-type copy, leads to gene replacement and inactivation of the corresponding polypeptide.

F. Disruption of Chromosomal S. aureus trxB Gene

Figure 4:
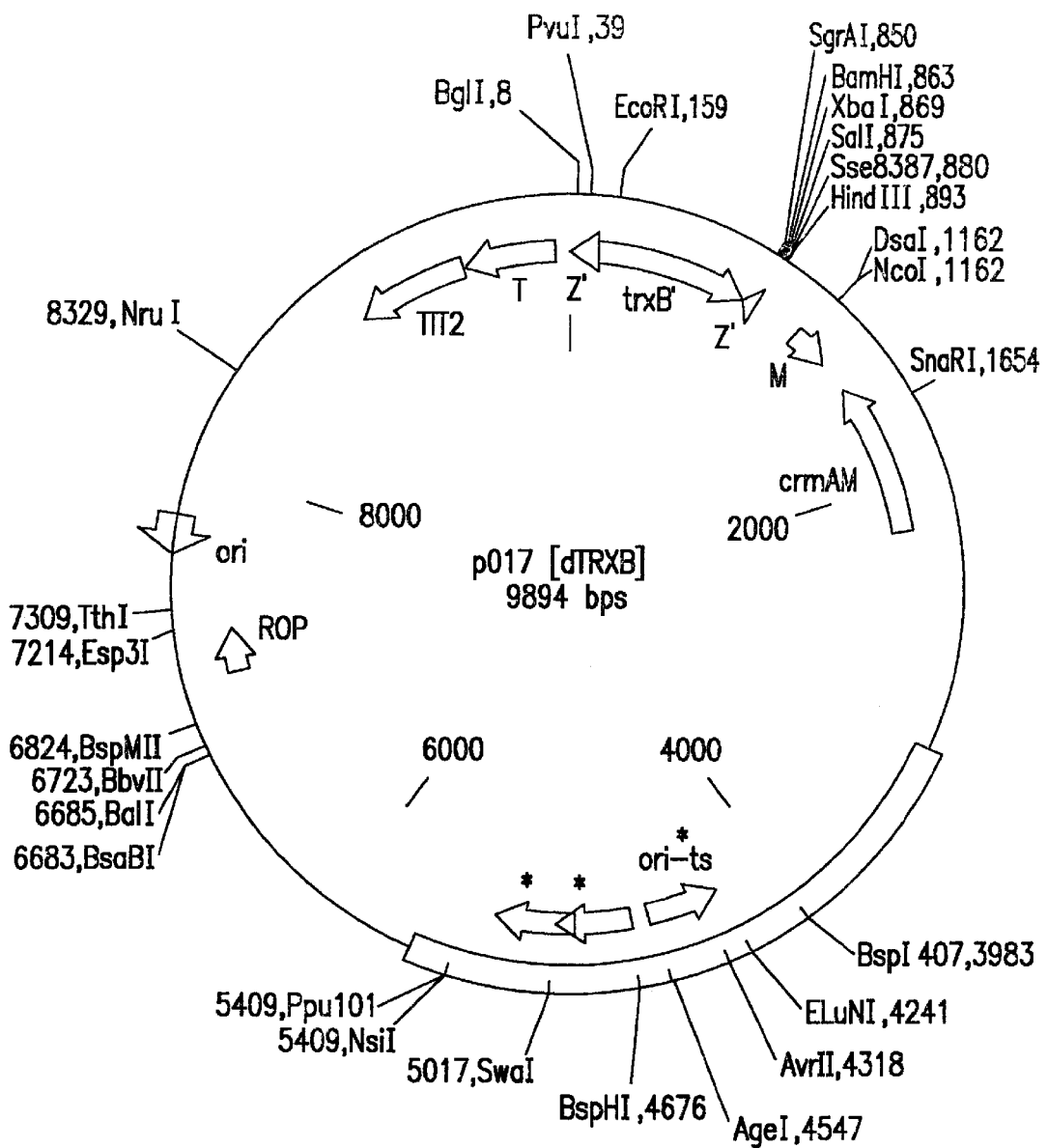
FIG. 4 is a diagram of disruption vector pOI7.

The disruption plasmid, pOI7 (FIG. 4), was made as follows. The PCR 700 bp internal trxB fragment was excised from plasmid pOI1 by digestion with BamHI and EcoI within the multiple cloning site, and inserted into pAUL-A to form pOI7. S. aureus strain RN4220 was transformed with pOI7 by electroporation, as described by Schenk, S. and Laddaga, A. (1992) Microbiol. Lett. 94:133–138, and transformants grown at 30° C. or 42° C. (the non-permissive temperature) on plates containing erythromycin. Transformants containing a mutant trxb gene due to disruption of the chromosomal gene were selected for directly at 42° C. From some 2000 transformants tested in this way, four grew up at 42° C. but only one could be further propagated at this temperature. PCR analysis revealed that in this case, and in other cases like it, no evidence was found for stable integration of the disruption vector at the chromosomal trxB locus. This supports the view that disruption of trxB is a lethal event. Control experiments using the pAUL-A plasmid containing a 800 bp internal segment of the S. aureus glnA gene, showed that stable integrants of the plasmid readily occurred at the glnA chromosomal locus.

G. Replacement of Chromosomal S. aureus trxB Gene

Figure 5A:
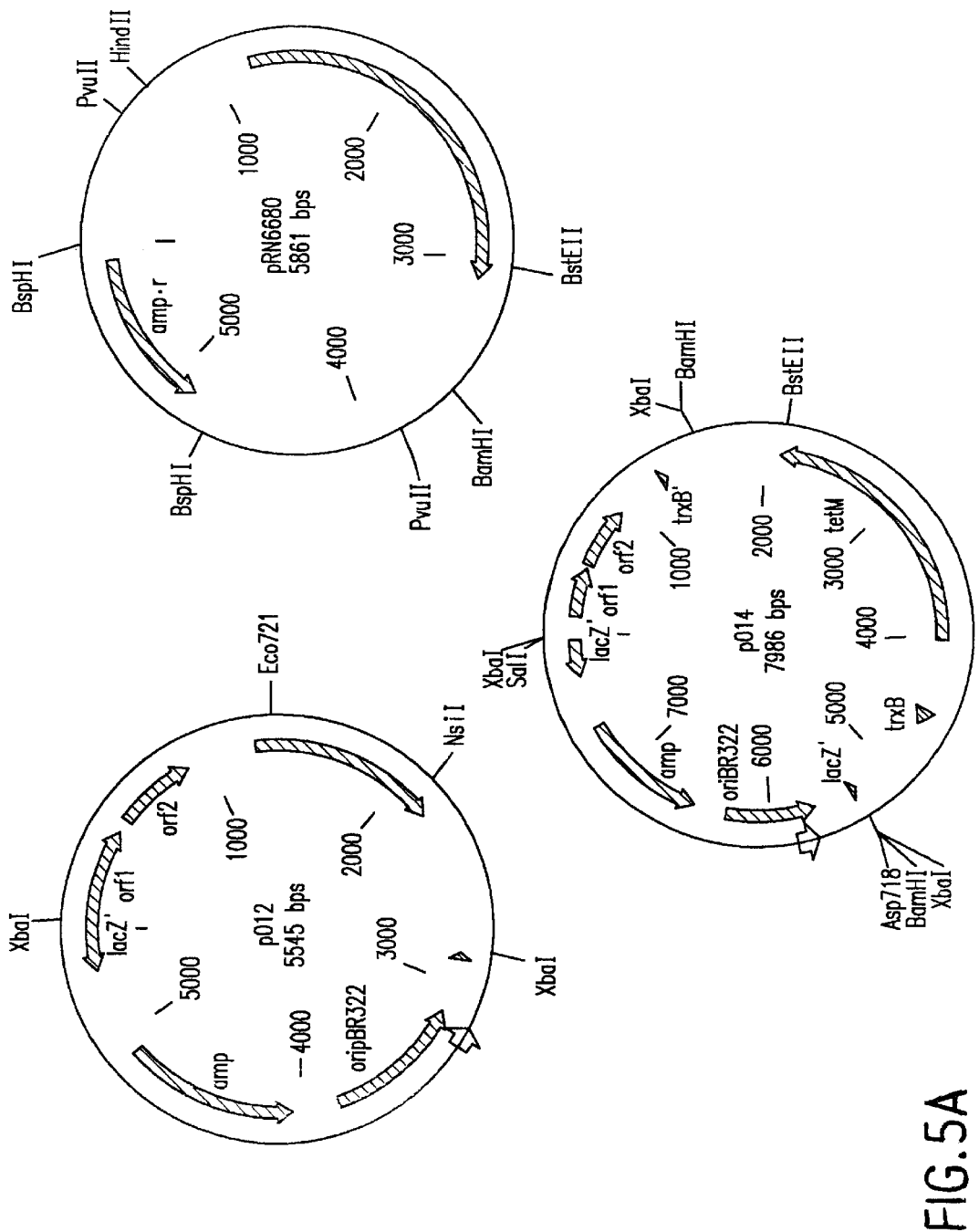
FIGS. 5A and 5B show the method used to construct the gene replacement vector pOI5.
Figure 5B:
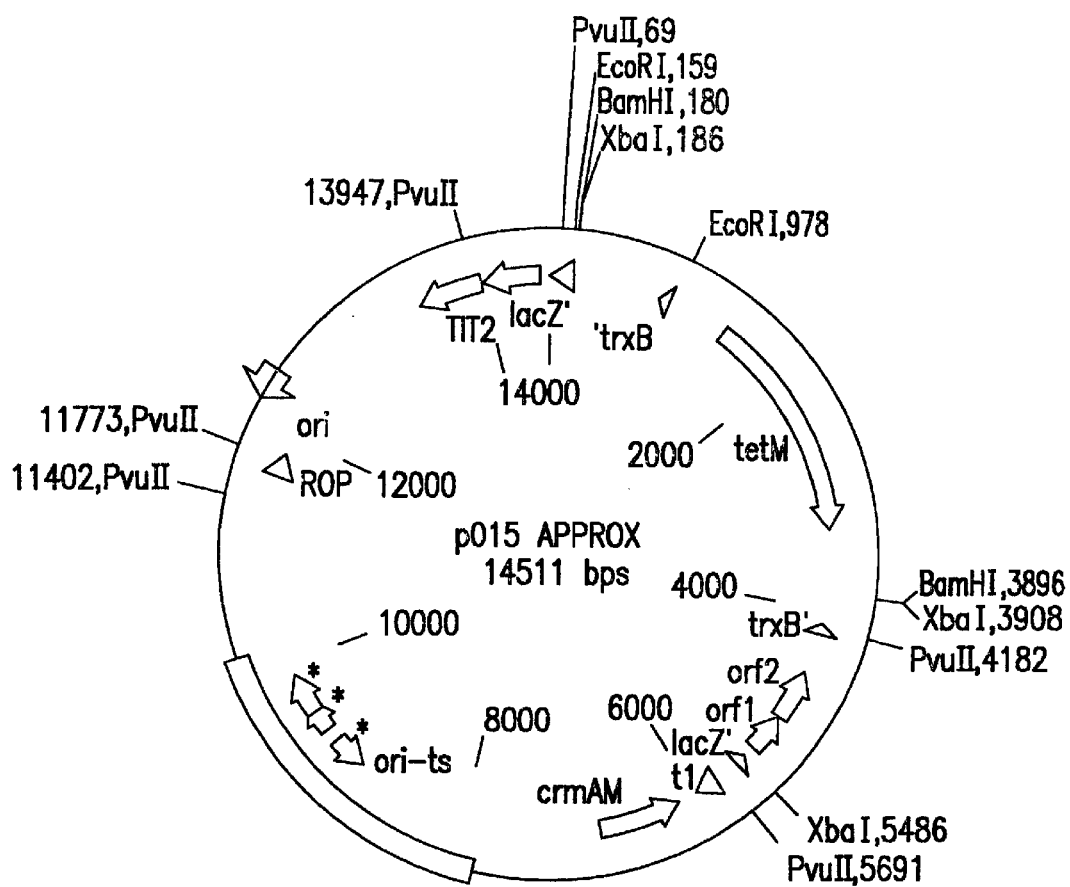

The replacement plasmid was made as follows (see FIGS. 5A and 5B). The 3.1 kb PvuII-HindII tetM (tetracycline resistance) cassette of pRN6680 (Nesin, et al. (1990) Antimicro. Agents. Chemother. 34:2273–2276) was blunt end ligated to the NruI/Eco721 large fragment of plasmid pOI2 to form pOI4 (FIG. 5A). Plasmid pOI2 is pUC18 containing the 2.8 kB trxB XbaI DNA fragment, as described above. Plasmid pOI4 lacks a large internal segment of the trxB gene. The 5.2 kB Asp718-SalI fragment of pOI4 was inserted into pAUL-A and the resulting plasmid, pOI5 (FIG. 5B) was used to transform by electroporation S. aureus RN4220. Transformants were grown at 42° C. in the presence of erythromycin and tetracycline. The DNAs of six randomly chosen transformants were analyzed by PCR and it was found in each case that the plasmid had integrated into the chromosome by a single crossover event in the DNA flanking region upstream of the trxB gene.

Phage ØI1 transduction was performed to generate the desired gene replacement, as described by Novick, R. P. Meth. Enzymology 204:587–636. The phage was grown on one of the above integrants at 42° C. in the presence of tetracycline and erythromycin and the lysate used to transduce S. aureus RN4220. Transductants, in which the wild-type copy of trxB had been replaced with the mutant copy due to a phage mediated double crossover recombination event, were screened for at 42° C. on plates containing tetracycline but lacking erythromycin. None of the 750 transductants scored in this way were found to have lost the plasmid erythromycin marker. PCR analysis showed that the transductants contained both the intact and wild-type trxb copies. Alternatively, one of the above integrant strains was propagated for 100 generations (in the presence of tetracycline and absence of erythromycin) to enable spontaneous elimination of either the wild-type or mutant trxB copies. None of the 750 clones tested were found to have lost the erythromycin marker. These results indicate that loss of the wild-type trxB gene is a lethal event and are consistent with the gene disruption experiments described above.

EXAMPLE 4

Identification of Genes Encoding Thioredoxin Reductase in Staphylococcus epidermidis The polypeptide sequence of TrxB from S. aureus shown in FIG. 2 (and designated hereinafter of TrxB_Sa) was used to search for genes having similar sequences (and thus theoretically the same functional activity as S. aureus TrxB) in a variety of microorganisms. The database search tool BLAST (Altschul, et al. (1990) J. Mol. Biol. 215:403410) was employed to search the PathoSeq™ database, version 3.0 (Incyte Pharmaceuticals, Palo Alto, Calif.). Matches were found in the genomic sequence of Staphylococcus epidermidis O-47 (available from Incyte) in the contiguous sequence (contig) designated SEP1c0392. The open reading frame encoding the entire TrxB in the contig was identified and the corresponding polypeptide product deduced. The gene for TrxB in S. epidermidis (designated trxB_Se) is shown in FIG. 6 (SEQ ID NO:9). TrxB_Sa and TrxB_Se were compared by aligning the full-length amino acid sequences using the GAP program. This program considers all possible alignments and gap positions and creates the alignment with the largest number of matched bases and the fewest gaps. A gap creation penalty and gap extension penalty is provided in units of matched bases. The program then creates a gap creation penalty number of matches for each gap it inserts. If a gap extension penalty greater than zero is used, the program also tracks, for each gap inserted, the length of the gap times the gap extension penalty. The GAP program uses the alignment method of Needleman and Wunsch (1970) J. Mol. Biol. 48:443453.

The alignment of TrxB_Se and TrxB_Sa is shown in FIG. 7. The sequences show about 90.4% identity and about 93.6% similarity (e.g., conservative amino acid substitutions). The gap weight was 12, length weight 4, quality 1470, ratio 4.727, average match 2.912, average mismatch –2.003, and gaps 0.

EXAMPLE 5

Cloning of the S. epidermidis trxB Gene and Overexpression in E. coli

The open reading frame encoding the polypeptide TrxB_Se is amplified by PCR from genomic DNA of S. epidermidis O-47 using the N-terminal primer 5'-GGGAATTCCATATGACTGAAGTAGATTTTGAT-3' (SEQ ID NO:7) and the C-terminal reverse primer 5'-CCCAAGCTTTTAATTATCTTTTAATTCTGT-3' (SEQ ID NO:8). The resulting amplified fragment is digested with the enzymes NdeII and HindIII and ligated with the vector pET22B(+) (Novagen, Madison Wis.) digested with the same enzymes. The resulting plasmid, designated pTRSE, in introduced in E. coli BL21 (DE3) essentially as in Example 3D. The E. coli strain carrying pTRSE is grown and the TrxB_Se enzyme is isolated essentially as described in Example 3D and analyzed as in Example 1.

EXAMPLE 6

Inactivation of trxB_Se

A 750 bp segment internal to trxB_Se, corresponding to nt 11471–12221, lacking N-terminal and C-terminal sequences coding for essential trxB nucleotide binding domains, is amplified by PCR employing the primers 5'-GGGAATTCGTATATGCATCTCGTGCCAAT-3' (SEQ ID NO:7) which contains an EcoRI site near the 5' end and 5'-CCCAATTGTACCTCGTACTTTAGTACTCA-3' (SEQ ID NO:8) which contains a HindIII site near the 5' end. The amplified fragment is digested with the enzymes EcoRI and HindIII, and ligated into the vector pAUL-A which is digested with the same enzymes. The resulting plasmid, designated pTRSE-int, is introduced into E. coli. The E. coli strain carrying pTRSE-int is grown and harvested and the plasmid pTRSE-int isolated. The plasmid is electroporated into S. epidermidis following the procedures described in Augustin, J. and Goetz, F. (1990) FEMS Microbiol. Lett. 68:203–208, employing selection for erythromycin resistance. A culture of S. epidermidis/pTRSE-int is grown to mid-log phase in the presence of erythromycin then placed on TSA plates containing erythromycin. To verify that trxB_Se is an essential gene for growth, the plates are incubated at 42° C. and the surviving colonies analyzed for integration of the pTRSE-int plasmid at the chromosomal trxB locus due to a single recombinational crossover event. Inability to isolate cells containing a disrupted trxB gene indicates that trxB_Se is an essential gene for growth.

EXAMPLE 7

High Throughput Assay to Identify Inhibitors of a Microbial Thioredoxin Reductase An insulin assay (modified from A. Holmgren and M. Bjornstedt, (1995) Methods in Enzymology 252:199–208) is used as a sensitive method to monitor the redox-activity of thioredoxin (T) in enabling the NADPH-dependent reduction of insulin disulfides in the presence of thioredoxin reductase (TrxB). In this reaction, TrxB specifically reduces $T-S_2$ to $T-(SH)_2$ using NADPH [reaction (1)]. The formed $T-(SH)_2$ is a powerful reductant of native insulin [reaction (2)].

TrxB

$$T\text{-}S_2 + NADPH + H^+ \longrightarrow T\text{-}(SH_2) + NADP^+ \quad (1)$$

Spontaneous

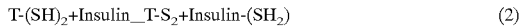

$$T\text{-}(SH)_2 + \text{Insulin} \longrightarrow T\text{-}S_2 + \text{Insulin-}(SH_2) \quad (2)$$

The amount of reduced insulin is determined spectrophotometrically at 412 nm after denaturation with 6M guanidine-HCl in the presence of DTNB step 1 in scheme. The reduction of insulin in a reaction that is T-dependent and TrxB-independent is tested spectrophotometrically at 650 nm as an increase in turbidity due to the precipitation of the free (reduced) insulin chain B, step 2 in scheme.

A. Step I:

One hundred μl of a reaction mixture containing 0.3 mM insulin, 100 mM HEPES pH 7.5, 3 mM EDTA, 0.5 NADPH, and 1–20 μg of S. aureus TrxB is added to the wells of a series of 96 well microtiter plates. Thioredoxin is omitted from well 1. Wells 3 through 94 contain one of the following: a few μg of the test compound singly, either as a dry powder or in 1–5 μl of 50 mM Tris-HCl, pH 7.8, 50 mM NaCl buffer; a few μg each of a mixture of the test compounds either as a dry powder or in a few μl of 50 mM Tris-HCl, pH 7.8, 50 mM NaCl buffer, for uncharacterized mixtures of compounds derived from bacteria, fungi, plants, marine organisms and present in a few μl of water, buffer, or DMSO. In the first two cases, the amount of compound employed is adjusted so that after all the additions are made the concentration of each compound is in the range of 1–10 μM. Wells 95 and 96 do not contain any compound. To well 1 and to wells 3–96 is added 10 μl of S. aureus TrxB solution containing approximately 300 pmoles in order to start the reaction. Water is added before the addition of TrxB to adjust the volume of each well to 150 μl. The plate is incubated at 37° C. for 20 min. The reaction is terminated by the addition of 150 μl of 0.4 mg/ml DTNB/6 M guanidine hydrochloride in 0.2 M Tris-HCl, pH 8.0 and the absorbance at 412 nm is measured. All compounds that show inhibition of the DTNB reaction are further tested in step II.

B. Step II:

(Modified) from A. Holmgren (1979) J. Biol. Chem. 254:9627–9632)

Two hundred and fifty μl of the assay mixture containing a freshly prepared solution of bovine insulin, 1 mg/ml of 0.1 M potassium phosphate pH 7.0, 2 mM EDTA, is added to all the wells of a series of 96 well microtiter plates. Thioredoxin solution, 10 μl, is added to wells 3–96 to reach 3–8 μM concentration. Wells 3 through 94 also contain one of the following samples that exhibited inhibition of the DTNB reaction in step I: a few μg of single compounds either as a dry powder or in 1–5 μl of 50 mM Tris-HCl, pH 7.8, 50 mM NaCl buffer, a few μg of a mixture of compounds either as a dry powder or in a few μl of 50 mM Tris-HCl, pH 7.8, 50 mM NaCl buffer; uncharacterized mixtures of compounds derived from bacteria, fungi, plants, marine organisms in a few μl of water, buffer, or DMSO. In the first two cases, the amount of compound employed is adjusted so that after all the additions are made, the concentration of each is in the range of 1–10 μM. Wells 95 and 96 do not contain any compound or extract. The reaction is started by the addition of 10 μl dithiothreitol (DTT) to wells 2–95 to reach a final concentration of 0.3–0.5 mM. The plate is thoroughly agitated and placed in a plate reader and the absorbance at 650 nm is determined. The absorbance is read at intervals of 0.5 min for 80 min. In a typical reaction in the control well 2, containing only DTT and insulin, no precipitation is observed until after about 70 min. In the presence of T and DTT, precipitation appears after 10–15 min.

Figure 8:
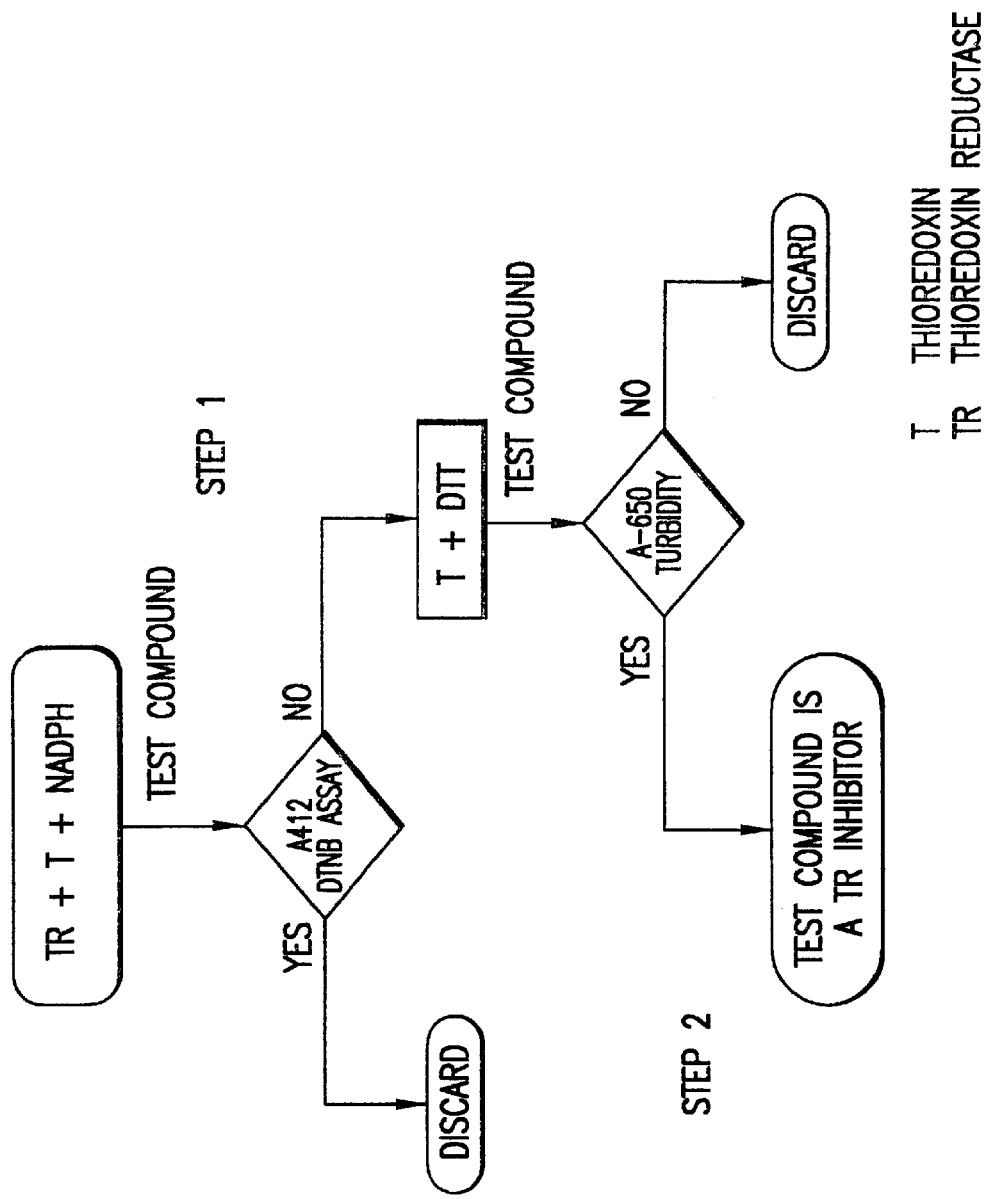
FIG. 8 is a flow chart depicting a method for identifying TrxB inhibitors using an insulin turbidity test.

In order to evaluate whether a compound is a potential TrxB inhibitor, the compound should exhibit the properties depicted in the flow chart shown as FIG. 8.

Thus, an isolated S. aureus TrxB polypeptide, DNA coding therefor and methods of using the same to identify inhibitors of TrxB, are provided. Although preferred embodiments of the subject invention have been described in some detail, it is understood that obvious variations can be made without departing from the spirit and the scope of the invention as defined by the appended claims.

We claim:

1. An isolated Staphyloocccus thioredoxin reductase (TrxB) polypeptide comprising an amino acid sequence having Staphylococcus thioredoxin reductase activity selected from the group consisting of: the amino acid sequence of SEQ ID NO:2 and an amino acid sequence having 90% identity to SEQ ID NO:2.

2. The polypeptide of claim 1, wherein the peptide sequence is SEQ ID NO:10.

3. An isolated polynucleotide encoding a Staphylococcus TrxB polypeptide comprising an amino acid sequence having Staphylococcus thioredoxin reductase activity, wherein the polynucleotide is selected from the group consisting of: the nucleotide sequence of SEQ ID NO:1 and a nucleotide sequence having 90% identity to SEQ ID NO:1.

4. A recombinant vector comprising the polynucleotide of claim 3 operably linked to control sequences that direct the transcription of the polynucleotide whereby said polynucleotide is expressed in a host cell.

5. A host cell comprising the vector of claim 4.

6. A method of producing a Staphylococcus TrxB polypeptide comprising:
   culturing the host cell of claim 5 under conditions that allow the production of the TrxB polypeptide; and
   recovering the TrxB polypeptide.

7. An isolated polynucleotide encoding a Staphylococcus TrxB polypeptide comprising amino acid sequence having Staphylococcus thioredoxin reductase activity, wherein the nucleotide sequence is SEQ ID NO:9.

8. A diagnostic test kit for detecting the presence of Stphylococcus in a test sample, comprising:

(a) a Staphylococcus TrxB polypeptide comprising an amino acid sequence having Saphylococcus thioredoxin reductase activity selected from the group consisting of: the amino acid sequence of SEQ ID NO:2 and an amino acid sequence having 90% identity to SEQ ID NO:2;

(b) one or more reagents for detecting the presence of Staphylococcus in a test sample; and (c) instructions for conducting the diagnostic test.

* * * * *

UNITED STATES PATENT AND TRADEMARK OFFICE
CERTIFICATE OF CORRECTION

PATENT NO.    : 6,767,536 B1
DATED         : July 27, 2004
INVENTOR(S)   : Aharonowitz et al.

It is certified that error appears in the above-identified patent and that said Letters Patent is hereby corrected as shown below:

Column 31,
Line 60, after "An isolated", delete "Staphylooccus" and insert -- Staphylococcus --.

Column 33,
Line 12, before "in a test sample, comprising:", delete "Stphylococcus" and insert -- Staphylococcus --.

Column 34,
Line 2, after "amino acid sequence having", delete "Saphylococcus" and insert -- Staphylococcus --.

Signed and Sealed this

Fifth Day of October, 2004

JON W. DUDAS
*Director of the United States Patent and Trademark Office*

SEQUENCE LISTING

<160> NUMBER OF SEQ ID NOS: 10

<210> SEQ ID NO 1
<211> LENGTH: 936
<212> TYPE: DNA
<213> ORGANISM: Staphylococcus aureus

<400> SEQUENCE: 1

-continued

```
atgactgaaa tagattttga tatagcaatt atcggtgcag gtccagctgg tatgactgct    60
gcagtatacg catcacgtgc taatttaaaa acagttatga ttgaaagagg tattccaggc   120
ggtcaaatgg ctaatacaga agaagtagag aacttccctg gtttcgaaat gattacaggt   180
ccagatttat ctacaaaaat gtttgaacac gctaaaaagt ttggtgcagt ttatcaatat   240
ggagatatta atctgtaga agataaaggc aatataaag tgattaactt tggtaacaaa     300
gaattaacag ctaaagcggt cattattgct acaggtgcag aatacaagaa aattggtgtt   360
ccgggtgaac aagaacttgg tggacgcggt gtaagttatt gtgcagtatg tgatggtgca   420
ttctttaaaa ataaacgcct attcgttatc ggtggtggtg actcagcagt agaagaggga   480
acattcttaa ctaaatttgc tgacaaagta acaatcgttc accgtcgtga tgagttacgt   540
gcacaacgta ttttacaaga tagagcattc aaaaatgata aaatagactt tatttggagc   600
catactttga aatcaattaa tgaaaaagac ggcaaagtgg gttctgtgac attaacgtct   660
acaaaagatg gttcagaaga aacacacgag gctgatggtg tattcatcta tattggtatg   720
aaaccattaa cagcaccatt taaagactta ggtattacaa atgatgttgg ttatattgtg   780
acaaaagatg atatgacaac atcagtacca ggtattttg cagcaggaga tgttcgcgac    840
aaaggtttac gccaaattgt cactgctact ggcgatggta gtattgcagc acaaagtgca   900
gcggaatata ttgaacattt aaacgatcaa gcttaa                             936
```

<210> SEQ ID NO 2
<211> LENGTH: 311
<212> TYPE: PRT
<213> ORGANISM: Staphylococcus aureus
<400> SEQUENCE: 2

```
Met Thr Glu Ile Asp Phe Asp Ile Ala Ile Gly Ala Gly Pro Ala
 1               5                  10                  15

Gly Met Thr Ala Ala Val Tyr Ala Ser Arg Ala Asn Leu Lys Thr Val
            20                  25                  30

Met Ile Glu Arg Gly Ile Pro Gly Gly Gln Met Ala Asn Thr Glu Glu
        35                  40                  45

Val Glu Asn Phe Pro Gly Phe Glu Met Ile Thr Gly Pro Asp Leu Ser
    50                  55                  60

Thr Lys Met Phe Glu His Ala Lys Lys Phe Gly Ala Val Tyr Gln Tyr
65                  70                  75                  80

Gly Asp Ile Lys Ser Val Glu Asp Lys Gly Glu Tyr Lys Val Ile Asn
                85                  90                  95

Phe Gly Asn Lys Glu Leu Thr Ala Lys Ala Val Ile Ile Ala Thr Gly
            100                 105                 110

Ala Glu Tyr Lys Lys Ile Gly Val Pro Gly Glu Gln Glu Leu Gly Gly
        115                 120                 125

Arg Gly Val Ser Tyr Cys Ala Val Cys Asp Gly Ala Phe Phe Lys Asn
    130                 135                 140

Lys Arg Leu Phe Val Ile Gly Gly Gly Asp Ser Ala Val Glu Glu Gly
145                 150                 155                 160

Thr Phe Leu Thr Lys Phe Ala Asp Lys Val Thr Ile Val His Arg Arg
                165                 170                 175

Asp Glu Leu Arg Ala Gln Arg Ile Leu Gln Asp Arg Ala Phe Lys Asn
            180                 185                 190

Asp Lys Ile Asp Phe Ile Trp Ser His Thr Leu Lys Ser Ile Asn Glu
        195                 200                 205
```

```
Lys Asp Gly Lys Val Gly Ser Val Thr Leu Thr Ser Thr Lys Asp Gly
    210                 215                 220
Ser Glu Glu Thr His Glu Ala Asp Gly Val Phe Ile Tyr Ile Gly Met
225                 230                 235                 240
Lys Pro Leu Thr Ala Pro Phe Lys Asp Leu Gly Ile Thr Asn Asp Val
                245                 250                 255
Gly Tyr Ile Val Thr Lys Asp Asp Met Thr Thr Ser Val Pro Gly Ile
                260                 265                 270
Phe Ala Ala Gly Asp Val Arg Asp Lys Gly Leu Arg Gln Ile Val Thr
            275                 280                 285
Ala Thr Gly Asp Gly Ser Ile Ala Ala Gln Ser Ala Ala Glu Tyr Ile
        290                 295                 300
Glu His Leu Asn Asp Gln Ala
305                 310
```

<210> SEQ ID NO 3
<211> LENGTH: 32
<212> TYPE: DNA
<213> ORGANISM: Artificial Sequence
<220> FEATURE:
<223> OTHER INFORMATION: N-terminal region primer
<221> NAME/KEY: misc_feature
<222> LOCATION: (3)...(3)
<223> OTHER INFORMATION: n = inosine at position 3
<221> NAME/KEY: misc_feature
<222> LOCATION: (6)...(6)
<223> OTHER INFORMATION: n = inosine at position 6
<221> NAME/KEY: misc_feature
<222> LOCATION: (9)...(9)
<223> OTHER INFORMATION: n = inosine at position 9
<221> NAME/KEY: misc_feature
<222> LOCATION: (12)...(12)
<223> OTHER INFORMATION: n = inosine at position 12

<400> SEQUENCE: 3
acnacngang tngaagaact ttctccagct gg                                    32

<210> SEQ ID NO 4
<211> LENGTH: 30
<212> TYPE: DNA
<213> ORGANISM: Artificial Sequence
<220> FEATURE:
<223> OTHER INFORMATION: C-terminal region primer
<221> NAME/KEY: misc_feature
<222> LOCATION: (6)...(6)
<223> OTHER INFORMATION: n = inosine at position 6
<221> NAME/KEY: misc_feature
<222> LOCATION: (9)...(9)
<223> OTHER INFORMATION: n = inosine at position 9
<221> NAME/KEY: misc_feature
<222> LOCATION: (12)...(12)
<223> OTHER INFORMATION: n = inosine at position 12

<400> SEQUENCE: 4
acgtcnccng cngcagaaag ctacagctcc                                       30

<210> SEQ ID NO 5
<211> LENGTH: 9
<212> TYPE: PRT
<213> ORGANISM: Artificial Sequence
<220> FEATURE:
<223> OTHER INFORMATION: Primer

<400> SEQUENCE: 5

Thr Glu Glu Val Glu Asn Phe Pro Gly
 1               5

<210> SEQ ID NO 6
<211> LENGTH: 7
<212> TYPE: PRT
<213> ORGANISM: Artificial Sequence
<220> FEATURE:
<223> OTHER INFORMATION: Primer

<400> SEQUENCE: 6

Gly Ile Phe Ala Ala Gly Asp
 1               5

<210> SEQ ID NO 7
<211> LENGTH: 32
<212> TYPE: DNA
<213> ORGANISM: Artificial Sequence
<220> FEATURE:
<223> OTHER INFORMATION: N-terminal primer

<400> SEQUENCE: 7
gggaattcca tatgactgaa atagattttg at                              32

<210> SEQ ID NO 8
<211> LENGTH: 27
<212> TYPE: DNA
<213> ORGANISM: Artificial Sequence
<220> FEATURE:
<223> OTHER INFORMATION: C-terminal primer

<400> SEQUENCE: 8
cccaagcttt taagcttgat cgtttaa                                    27

<210> SEQ ID NO 9
<211> LENGTH: 933
<212> TYPE: DNA
<213> ORGANISM: Staphylococcus epidermidis

<400> SEQUENCE: 9
atgactgaag tagattttga tgtagcaata atcggtgcag gtcctgccgg tatgacagca    60
gcagtatatg catctcgtgc caatttaaaa actgtcatca ttgaacgcgg tatgccaggc   120
ggtcaaatgg caaacactga agaagtagag aattttccag gatttgagat gatcacaggt   180
cctgacttat ctactaaaat gtttgaacat gctaaaaaat ttggtgcgga ataccaatat   240
ggcgatatta atctgttga agataaaggc gactataaag ttatcaattt agggaataaa   300
gagataacag cacatgcagt tattatctca actggagcag agtataaaaa gattggcgtt   360
cctggtgaac aagaattagg aggacgtgga gtaagttatt gtgcggtttg tgatggagca   420
ttctttaaaa ataaacgtct tttcgtaatt ggcggcggag attcagcggt agaagaaggt   480
actttcttaa ctaaatttgc agataaagta acgattgttc accgtagaga tgaattacgt   540
gcacaaaaca tcttgcaaga acgtgccttc aaaaatgata agttgactt tatttggagt   600
catacactta aaacaattaa tgaaaagat ggtaaagttg gttcagttac acttgaatca   660
actaaagatg gtgctgaaca gacttatgat gccgacggtg tattcattta tattggaatg   720
aaaccactca cagcaccatt taaaaatctt ggtattacaa atgacgcggg atacattgtc   780
acacaagatg cacatgagtac taagtacga ggtattttg ctgcaggtga cgttcgtgat   840
aaagggttac gtcaaattgt tactgctaca ggagacggta gtattgcggc tcaaagtgca   900
gctgattata ttacagaatt aaaagataat taa                              933

```
<210> SEQ ID NO 10
<211> LENGTH: 310
<212> TYPE: PRT
<213> ORGANISM: Staphylococcus epidermidis

<400> SEQUENCE: 10

Met Thr Glu Val Asp Phe Asp Val Ala Ile Ile Gly Ala Gly Pro Ala
1               5                   10                  15

Gly Met Thr Ala Ala Val Tyr Ala Ser Arg Ala Asn Leu Arg Thr Val
            20                  25                  30

Met Ile Glu Arg Gly Met Pro Gly Gly Gln Met Ala Asn Thr Glu Glu
        35                  40                  45

Val Glu Asn Phe Pro Gly Phe Glu Met Ile Thr Gly Pro Asp Leu Ser
    50                  55                  60

Thr Lys Met Phe Glu His Ala Lys Lys Phe Gly Ala Glu Tyr Gln Tyr
65                  70                  75                  80

Gly Asp Ile Lys Ser Val Glu Asp Lys Gly Asp Tyr Lys Val Ile Asn
                85                  90                  95

Leu Gly Asn Lys Glu Ile Thr Ala His Ala Val Ile Ile Ser Thr Gly
            100                 105                 110

Ala Glu Tyr Lys Lys Ile Gly Val Pro Gly Glu Gln Glu Leu Gly Gly
        115                 120                 125

Arg Gly Val Ser Tyr Cys Ala Val Cys Asp Gly Ala Phe Phe Lys Asn
    130                 135                 140

Lys Arg Leu Phe Val Ile Gly Gly Gly Asp Ser Ala Val Glu Glu Gly
145                 150                 155                 160

Thr Phe Leu Thr Lys Phe Ala Asp Lys Val Thr Ile Val His Arg Arg
                165                 170                 175

Asp Glu Leu Arg Ala Gln Asn Ile Leu Gln Glu Arg Ala Phe Lys Asn
            180                 185                 190

Asp Lys Val Asp Phe Ile Trp Ser His Thr Leu Lys Thr Ile Asn Glu
        195                 200                 205

Lys Asp Gly Lys Val Gly Ser Val Thr Leu Glu Ser Thr Lys Asp Gly
210                 215                 220

Ala Glu Gln Thr Tyr Asp Ala Asp Gly Val Phe Ile Tyr Ile Gly Met
225                 230                 235                 240

Lys Pro Leu Thr Ala Pro Phe Lys Asn Leu Gly Ile Thr Asn Asp Ala
                245                 250                 255

Gly Tyr Ile Val Thr Gln Asp Asp Met Ser Thr Lys Val Arg Gly Ile
            260                 265                 270

Phe Ala Ala Gly Asp Val Arg Asp Lys Gly Leu Arg Gln Ile Val Thr
        275                 280                 285

Ala Thr Gly Asp Gly Ser Ile Ala Ala Gln Ser Ala Ala Asp Tyr Ile
    290                 295                 300

Thr Glu Leu Lys Asp Asn
305                 310
```